US009821091B2

(12) United States Patent
Hossainy et al.

(10) Patent No.: US 9,821,091 B2
(45) Date of Patent: Nov. 21, 2017

(54) METHODS OF TREATMENT OF POLYMERIC COATINGS FOR CONTROL OF AGENT RELEASE RATES

(71) Applicant: Abbott Cardiovascular Systems Inc., Santa Clara, CA (US)

(72) Inventors: Syed F. A. Hossainy, Hayward, CA (US); Fuh-Wei Tang, Temecula, CA (US); Lothar W. Kleiner, Los Altos, CA (US); Thierry Glauser, Redwood City, CA (US); Yiwen Tang, San Jose, CA (US); Wouter E. Roorda, Palo Alto, CA (US); Stephen D. Pacetti, San Jose, CA (US); Gina Zhang, Calabasas, CA (US); Yung-Ming Chen, San Jose, CA (US); Andrew F. McNiven, Temecula, CA (US); Sean A. McNiven, San Francisco, CA (US); Brandon J. Yoe, Temecula, CA (US)

(73) Assignee: Abbot Cardiovascular Systems Inc., Santa Clara, CA (US)

( * ) Notice: Subject to any disclaimer, the term of this patent is extended or adjusted under 35 U.S.C. 154(b) by 545 days.

(21) Appl. No.: 13/953,656

(22) Filed: Jul. 29, 2013

(65) Prior Publication Data
US 2014/0004250 A1 Jan. 2, 2014

Related U.S. Application Data

(62) Division of application No. 11/448,956, filed on Jun. 6, 2006, now abandoned.

(51) Int. Cl.
| A61L 31/10 | (2006.01) |
| A61L 27/40 | (2006.01) |
| A61L 27/44 | (2006.01) |
| A61L 27/50 | (2006.01) |
| A61L 27/54 | (2006.01) |
| A61L 31/12 | (2006.01) |
| A61L 31/14 | (2006.01) |
| A61L 31/16 | (2006.01) |

(52) U.S. Cl.
CPC .............. *A61L 31/10* (2013.01); *A61L 27/40* (2013.01); *A61L 27/44* (2013.01); *A61L 27/50* (2013.01); *A61L 27/54* (2013.01); *A61L 31/12* (2013.01); *A61L 31/14* (2013.01); *A61L 31/16* (2013.01); *A61L 2300/00* (2013.01)

(58) Field of Classification Search
CPC .................................................... A61L 31/10
See application file for complete search history.

(56) References Cited

U.S. PATENT DOCUMENTS

| 5,810,873 | A | 9/1998 | Morales |
| 5,893,852 | A | 4/1999 | Morales |
| 5,920,975 | A | 7/1999 | Morales |
| 5,972,016 | A | 10/1999 | Morales |
| 5,974,652 | A | 11/1999 | Kimes et al. |
| 6,024,737 | A | 2/2000 | Morales |
| 6,051,002 | A | 4/2000 | Morales |
| 6,082,990 | A | 7/2000 | Jackson et al. |
| 6,092,273 | A | 7/2000 | Villareal |
| 6,141,855 | A | 11/2000 | Morales |
| 6,202,272 | B1 | 3/2001 | Jackson |
| 6,240,615 | B1 | 6/2001 | Kimes et al. |
| 6,277,110 | B1 | 8/2001 | Morales |
| 6,481,262 | B2 | 11/2002 | Ching et al. |
| 6,510,722 | B1 | 1/2003 | Ching et al. |
| 6,743,462 | B1* | 6/2004 | Pacetti .......................... 427/2.24 |
| 7,056,591 | B1 | 6/2006 | Pacetti et al. |
| 7,125,516 | B2 | 10/2006 | Andersen et al. |
| 7,220,816 | B2 | 5/2007 | Pacetti et al. |
| 7,255,891 | B1 | 8/2007 | Pacetti |
| 7,285,304 | B1 | 10/2007 | Hossainy et al. |
| 7,335,314 | B2 | 2/2008 | Wu et al. |
| 7,435,788 | B2 | 10/2008 | Pacetti |
| 7,795,467 | B1 | 9/2010 | Pacetti et al. |
| 7,820,732 | B2 | 10/2010 | Tang et al. |
| 8,048,442 | B1 | 11/2011 | Hossainy et al. |
| 8,246,973 | B2 | 8/2012 | Hossainy et al. |
| 8,252,361 | B2 | 8/2012 | Kramer-Brown et al. |
| 8,293,318 | B1 | 10/2012 | Hsu et al. |
| 8,377,107 | B2 | 2/2013 | Kleiner et al. |
| 8,377,499 | B2 | 2/2013 | Kleiner et al. |
| 8,551,512 | B2 | 10/2013 | Hossainy et al. |
| 2002/0102674 | A1 | 8/2002 | Anderson |
| 2002/0188037 | A1 | 12/2002 | Chudzik et al. |
| 2005/0208091 | A1 | 9/2005 | Pacetti |
| 2005/0220839 | A1 | 10/2005 | DeWitt et al. |
| 2005/0226991 | A1 | 10/2005 | Hossainy et al. |
| 2005/0265960 | A1 | 12/2005 | Pacetti et al. |
| 2005/0271700 | A1 | 12/2005 | Desnoyer et al. |
| 2005/0288481 | A1* | 12/2005 | DesNoyer et al. ........... 528/310 |

(Continued)

FOREIGN PATENT DOCUMENTS

| WO | WO 97/44070 | 11/1997 |
| WO | WO 2004/087797 | 10/2004 |
| WO | WO 2005/046521 | 5/2005 |
| WO | WO 2005/089829 | 9/2005 |
| WO | WO 2006/019634 | 2/2006 |

OTHER PUBLICATIONS

U.S. Appl. No. 10/816,072, filed Mar. 31, 2004, Dugan et al.
Invitation to Pay Additional Fees for PCT/US2007/013396, dated Aug. 19, 2008, 10 pgs.
Brader et al., "Hybrid insulin cocrystals for controlled release delivery", Nature Biotechnology vol. 20, pp. 800/804 (2002).

(Continued)

Primary Examiner — Adam C Milligan
Assistant Examiner — Sarah Alawadi
(74) Attorney, Agent, or Firm — Squire Patton Boggs (US) LLP

(57) ABSTRACT

The present disclosure teaches methods of controlling the release rate of agents from a polymeric matrix. The methods relate to the application of pressure, and optionally, in combination with heat, to a polymeric coating.

19 Claims, 12 Drawing Sheets

(56) References Cited

U.S. PATENT DOCUMENTS

| | | |
|---|---|---|
| 2006/0115449 A1 | 6/2006 | Pacetti |
| 2006/0115513 A1 | 6/2006 | Hossainy et al. |
| 2007/0280988 A1 | 12/2007 | Ludwig et al. |
| 2007/0286882 A1 | 12/2007 | Tang et al. |
| 2008/0095918 A1 | 4/2008 | Kleiner et al. |
| 2008/0124372 A1 | 5/2008 | Tang et al. |
| 2009/0326645 A1 | 12/2009 | Pacetti et al. |
| 2011/0086162 A1 | 4/2011 | Hossainy et al. |
| 2011/0144741 A1 | 6/2011 | Kleiner et al. |
| 2011/0153004 A1 | 6/2011 | Kleiner et al. |

OTHER PUBLICATIONS

Chae Park et al., "Membrane formation by water vapor induced phase inversion", J. of Membrane Science 156, pp. 169/178 (1999).

Danesh et al., "Polymorphic Discrimination Using Atomic Force Microscopy: Distinguishing Between Two Polymorphs of the Drug Cimetidine", Langmuir 16, pp. 866/870 (2000).

Dev et al., *Kinetics of Drug Delivery to the Arterial Wall via Polyurethane/Coated Removable Nitinol Stent: Comparative Study of Two Drugs*, Catheterization and Cardiovascular Diagnosis 34:272/278 (1995).

Eigler et al., *Local Arterial Wall Drug Delivery from a Polymer Coated Removable Metallic Stent: Kinetics, Distribution, and Bioactivity of Forskolin*, JACC, 4A (701/1), Abstract (Feb. 1994).

Kutryk et al., *Coronary Stenting: Current Perspectives*, a companion to the Handbook of Coronary Stents 16 pgs. (1999).

Muller et al., *Advances in Coronary Angioplasty: Endovascular Stents*, Coron. Arter. Dis., 1(4), pp. 438/448 (Jul./Aug. 1990).

Ozaki et al., *New Stent Technologies*, Progress in Cardiovascular Diseases, vol. XXXIX(2):129/140 (Sep./Oct. 1996).

Peng et al., *Role of polymers in improving the results of stenting in coronary arteries*, Biomaterials 17:685/694 (1996).

Schatz, *A View of Vascular Stents*, Circulation, 79(2), pp. 445/457 (Feb. 1989).

Schierholz "Physico/chemical properties of a rifampicin/releasing polydimethyl/siloxane shunt", Biomaterials 18, pp. 635/641 (1997).

Singhal et al., "Drug polymorphism and dosage form design: a practical perspective", Advanced Drug Delivery Rev. 56, pp. 335/347 (2004).

Van Beusekom et al., *Coronary stent coatings*, Coronary Artery Disease 5(7):590/596 (Jul. 1994).

Variankaval et al., "Polymorphism of 17/βestradiol in a transdermal drug delivery system", J. of Mat. Science: Materials in Medicine 13, pp. 271/280 (2002).

Washburn et al., "Co/extrusion of biocompatible polymers for scaffolds with co/continuous morphology", J. of Biomed. Mat. Res. pp. 20/29 (2002).

Wilensky et al., *Methods and Devices for Local Drug Delivery in Coronary and Peripheral Arteries*, Trends Cardiovasc. Med. 3(5):163/170 (1993).

* cited by examiner

METHODS OF TREATMENT OF POLYMERIC COATINGS FOR CONTROL OF AGENT RELEASE RATES

RELATED APPLICATION

This application is a divisional application of U.S. application Ser. No. 11/448,956, filed on Jun. 6, 2006, and published as United States Patent Application Publication number 2008-0124372 A1, on May 29, 2008, which is hereby incorporated by reference herein for all purposes, and which is incorporated by reference herein in its entirety, including any drawings.

BACKGROUND

Field of the Invention

This invention is directed to the control of the morphologies within polymer matrices in facilitating the design of release rate profiles of agents from within these matrices.

Description of the State of the Art

Biomaterials research is continuously striving to improve the compositions from which medical articles, such as medical devices and coatings for medical devices, are produced. An example of a medical article is an implantable medical device.

A stent is an example of an implantable medical device that can benefit from improvements, such as a coating that can be used as a vehicle for delivering pharmaceutically active agents in a predictable manner. Stents can act as a mechanical intervention to physically hold open and, if desired, expand a passageway within a subject. Typically, a stent may be compressed, inserted into a small vessel through a catheter, and then expanded to a larger diameter once placed in a proper location. Examples of patents disclosing stents include U.S. Pat. Nos. 4,733,665, 4,800,882 and 4,886,062.

Stents play an important role in a variety of medical procedures such as, for example, percutaneous transluminal coronary angioplasty (PTCA), which is a procedure used to treat heart disease. In PTCA, a balloon catheter is inserted through a brachial or femoral artery, positioned across a coronary artery occlusion, inflated to compress atherosclerotic plaque and open the lumen of the coronary artery, deflated and withdrawn. Problems with PTCA include formation of intimal flaps or torn arterial linings, both of which can create another occlusion in the lumen of the coronary artery. Moreover, thrombosis and restenosis may occur several months after the procedure and create a need for additional angioplasty or a surgical by-pass operation. Stents are generally implanted to reduce occlusions, inhibit thrombosis and restenosis, and maintain patency within vascular lumens, such as the lumen of a coronary artery.

Stents are also being developed to provide a local delivery of agents. Local delivery of agents is often preferred over systemic delivery of agents, particularly where high systemic doses are necessary to achieve an effect at a particular site within a subject—high systemic doses of agents can often create adverse effects within the subject. One proposed method of local delivery includes coating the surface of a medical article with a polymeric carrier and attaching an agent to, or blending it with, the polymeric carrier.

Agent-coated stents have demonstrated dramatic reductions in the rates of stent restenosis by inhibiting tissue growth associated with the restenosis. Restenosis is a very complicated process and, agents have been applied, alone and in combination, in an attempt to circumvent the process. The process of restenosis in coronary artery disease is derived from a complex interplay of several implant-centered biological parameters. These are thought to be the combination of elastic recoil, vascular remodeling, and neointimal hyperplasia. Since restenosis is a multifactorial phenomenon, the local delivery of agents from a stent can be improved through the design of a release rate profile that would deliver agents as needed from the stent in a controlled and predictable manner. For example, one method of applying multiple agents involves blending the agents together in one formulation and applying the blend to the surface of a stent in a polymer matrix. A disadvantage of this method is that the agents are released from the matrix through a somewhat variable polymeric matrix morphology and, as such, compete with one another for release in an unpredictable manner. Other methods suffer from a sudden initial release of agents in high amounts, known as a burst release, which can prevent a prolonged release of agents in sufficient concentrations.

In some cases, polymeric matrices that are otherwise desirable are unable to meet particular performance characteristics that are required by some medical articles. Often, the inability to meet particular performance characteristics results from combining components that are desirable independently but form undesirable morphologies that cannot meet the required performance characteristics when formed into a polymeric matrix.

In other cases, polymeric matrices that are desirable upon manufacture can be unpredictable in performance at the time of use. Morphological changes are known to happen to medical articles during processing and storage, as well as after application in vivo. Unfortunately, the predictability of a medical article can rely on the ability to control these changes.

Those skilled in the art will appreciate a reliable way of controlling the performance of medical articles which includes controlling the release of agents, since a controlled release of agents can be critical to preventing, inhibiting, treating or mitigating a disease process. The ability to select and design the morphology of a polymeric matrix can not only provide for control over the release rate of agents but can also can assist in designing and maintaining the physical and mechanical properties of medical devices and coatings. Accordingly, control over the morphology of a polymeric matrix is an important design consideration and one of the next hallmarks in the development of novel medical articles.

SUMMARY

The present invention describes a method for creating a medical article. The article comprises a polymeric matrix having a predetermined initial morphology (IM) profile and an agent. The method includes selecting a desired IM profile; forming a polymeric layer comprising the agent on a surface of the medical article; and subjecting the polymeric layer to a terminal process step comprising:

exposing the polymeric layer to a fluid while forming the layer, wherein the composition of the fluid is preselected to be miscible or immiscible with a component in the polymeric layer;

applying a pressure to the polymeric layer;

applying a combination of heat and pressure to the polymeric layer; or a combination thereof; wherein the subjecting transforms the polymeric layer into a polymeric matrix having a predetermined IM profile.

In some embodiments, the present invention provides a method of creating a medical article having a desired rate of release of an agent, wherein the method comprises:

selecting a rate of release of an agent from a medical article having a polymeric matrix comprising the agent;

obtaining the agent in a desired form, or a combination of forms, that provides the selected rate of release through dissolution, diffusion, or a combination thereof; wherein, the form, or combination of forms, comprises a component selected from a group consisting of a polymorph, a solvate, a hydrate, and an amorphous form of the agent;

preparing a composition comprising a polymer and the agent;

applying the composition on the medical article to form a polymeric layer comprising the agent; and forming the polymeric matrix from the polymeric layer, wherein the polymeric matrix has the selected rate of release of the agent.

In some embodiments, the present invention provides a medical article comprising a polymeric matrix having a first component and a second component; wherein, the first component comprises a first polymer, the second component comprises an agent, and the polymeric matrix has a predetermined initial morphology (IM) profile. Some exemplary agents include, but are not limited to, paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), clobetasol, pimecrolimus, imatinib mesylate, midostaurin, prodrugs thereof, co-drugs thereof, or a combination thereof.

The coating can be formed on an implantable device such as a stent, which can be implanted in a patient to treat, prevent, mitigate, or reduce a vascular medical condition, or to provide a pro-healing effect. Examples of these conditions include atherosclerosis, thrombosis, restenosis, hemorrhage, vascular dissection or perforation, vascular aneurysm, vulnerable plaque, chronic total occlusion, claudication, anastomotic proliferation (for vein and artificial grafts), bile duct obstruction, ureter obstruction, tumor obstruction, or combinations of these.

DETAILED DESCRIPTION

As discussed in more detail below, the embodiments of the present invention generally encompass controlling the morphology of polymeric matrices to control their performance characteristics. More particularly, the present invention provides a method of forming a medical article having such a polymeric matrix to provide a controlled release of an agent from the medical article. A "medical article" can include, but is not limited to, a medical device or a coating for a medical device.

Examples of medical devices include, but are not limited to, stents, stent-grafts, vascular grafts, artificial heart valves, foramen ovale closure devices, cerebrospinal fluid shunts, pacemaker electrodes, guidewires, ventricular assist devices, cardiopulmonary bypass circuits, blood oxygenators, coronary shunts (AXIUS™, Guidant Corp.), vena cava filters, and endocardial leads (FINELINE® and ENDOTAK®, Guidant Corp.). In some embodiments, the stents include, but are not limited to, tubular stents, self-expanding stents, coil stents, ring stents, multi-design stents, and the like. In other embodiments, the stents are metallic; low-ferromagnetic; non-ferromagnetic; biostable polymeric; biodegradable polymeric or biodegradable metallic. In some embodiments, the stents include, but are not limited to, vascular stents, renal stents, biliary stents, pulmonary stents and gastrointestinal stents.

The medical devices can be comprised of a metal or an alloy, including, but not limited to, ELASTINITE® (Guidant Corp.), NITINOL® (Nitinol Devices and Components), stainless steel, tantalum, tantalum-based alloys, nickel-titanium alloy, platinum, platinum-based alloys such as, for example, platinum-iridium alloys, iridium, gold, magnesium, titanium, titanium-based alloys, zirconium-based alloys, alloys comprising cobalt and chromium (ELGILOY®, Elgiloy Specialty Metals, Inc.; MP35N and MP20N, SPS Technologies) or combinations thereof. The tradenames "MP35N" and "MP20N" describe alloys of cobalt, nickel, chromium and molybdenum. The MP35N consists of 35% cobalt, 35% nickel, 20% chromium, and 10% molybdenum. The MP20N consists of 50% cobalt, 20% nickel, 20% chromium, and 10% molybdenum. Medical devices with structural components that are comprised of bioabsorbable polymers or biostable polymers are also included within the scope of the present invention.

The control over the release of agents provides for control over, inter alia, the therapeutic, prophylactic, diagnostic, and ameliorative effects that are realized by a patient in need of such treatment. The terms "subject" and "patient" can be used interchangeably and refer to an animal such as a mammal including, but not limited to, non-primates such as, for example, a cow, pig, horse, cat, dog, rat, and mouse; and primates such as, for example, a monkey or a human.

Figure 1:
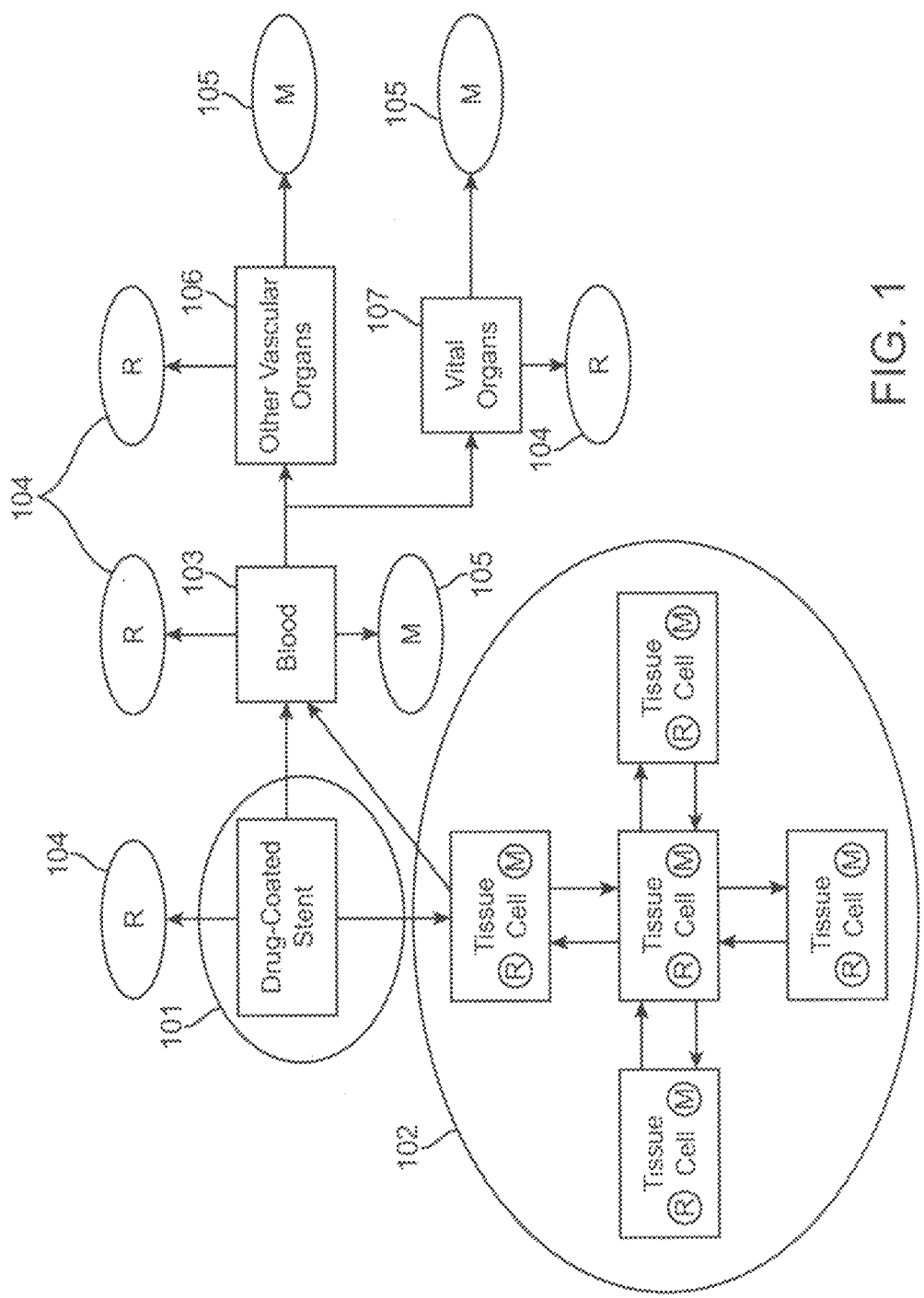
FIG. 1 is a diagram used to illustrate the local pharmacokinetics of agent release from a stent and its subsequent uptake in the coronary vasculature according to some embodiments of the present invention.

FIG. 1 is a diagram used to illustrate the local pharmacokinetics of agent release from a stent and its subsequent uptake in the coronary vasculature according to some embodiments of the present invention. In region 101, the agent that will be released from the stent is a drug. The agent can be released and passed through tissue cells within adjoining tissue 102, blood 103, or the agent can remain as residual agent ("R") 104 on the stent. The agent can also be metabolized ("M") 105 after its delivery to adjoining tissue 102, blood 103, other vascular organs 106, or vital organs 107. In addition, the control of the release rate of agents also has an effect upon the mechanical integrity of the polymeric matrix, as well as a relationship to a subject's absorption rate of the absorbable polymers.

Figure 2:
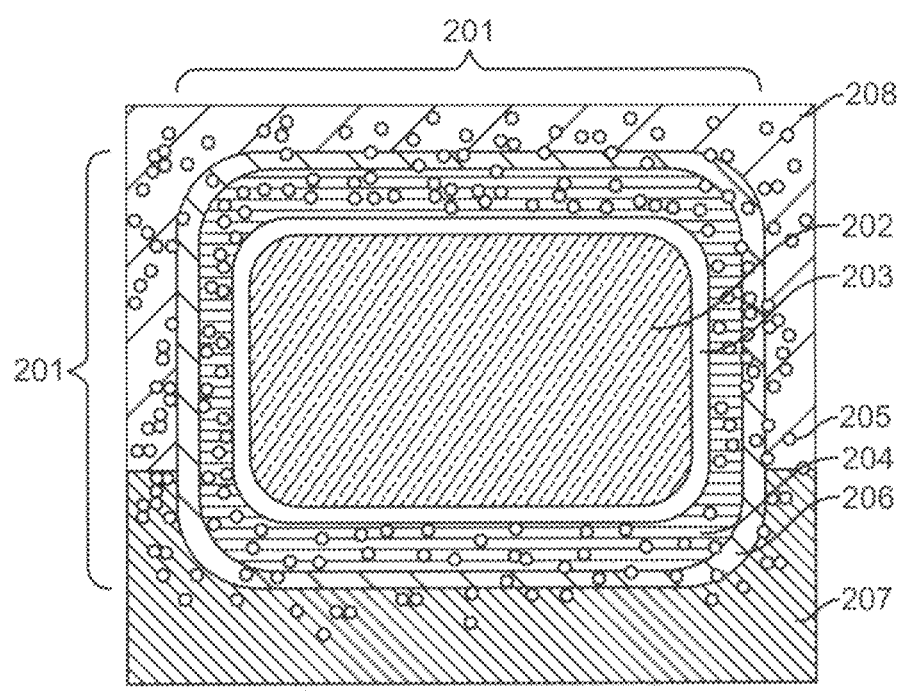
FIG. 2 illustrates a cross-section of a coating on a stent strut within a vascular organ according to some embodiments of the present invention.

FIG. 2 illustrates a cross-section of a coating on a stent strut within a vascular organ according to some embodiments of the present invention. The cross-section of the coated stent strut 201 includes a stent 202, an optional primer layer 203, a polymer matrix 204 that includes at least one agent 205, and an optional top-coat layer 206 that can further control the diffusion of the agent 205 out of the polymer matrix 204. The coated stent strut 201 is adjoining vascular tissue 207 and blood 208. The agent 205 is released from the polymer reservoir 204 into the blood 208 and the vascular tissue 207. This release of the agent 205 includes a diffusion parameter, so design of the polymeric matrix 204 can include diffusion considerations in order to further obtain control over the release of the agent 205.

In some embodiments, the invention is a method for creating a medical article, wherein the medical article includes a polymeric matrix having a predetermined initial morphology profile and an agent. The medical article can include a polymeric matrix having a predetermined initial morphology profile ("IM profile"), i.e. a predetermined arrangement of the components within the matrix, wherein at least one of these components includes an agent. It has been discovered that these predetermined IM profiles can be designed to provide a controllable release rate of agents from the polymeric matrix. The term "initial morphology" refers to the morphology of the polymeric matrix in its initial state after the medical article has been manufactured but before implantation.

The morphology of a polymeric matrix refers the way that the components of the matrix are arranged. In some embodiments, the morphology can include, for example, by the presence and characteristics of phase separations between components within the polymeric matrix, where the phase separation can exist between polymers, an agent and a polymer, between agents, or between other components in the polymeric matrix.

Figure 3B:
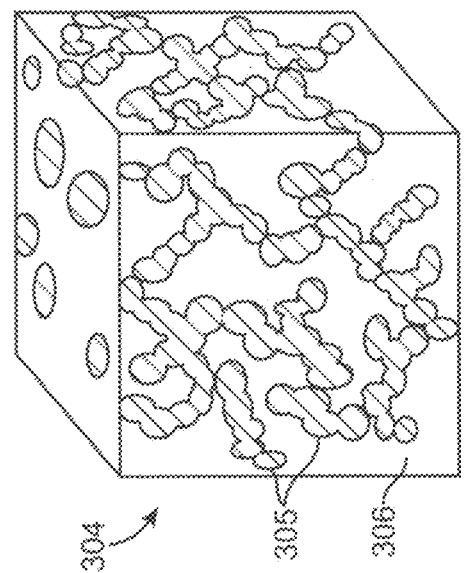
FIGS. 3a and 3b illustrate a section of a polymeric matrix having a morphology containing an agent-enriched phase at a concentration that is below about 30% by volume, and above about 30% by volume, respectively, according to some embodiments of the present invention.
Figure 3A:
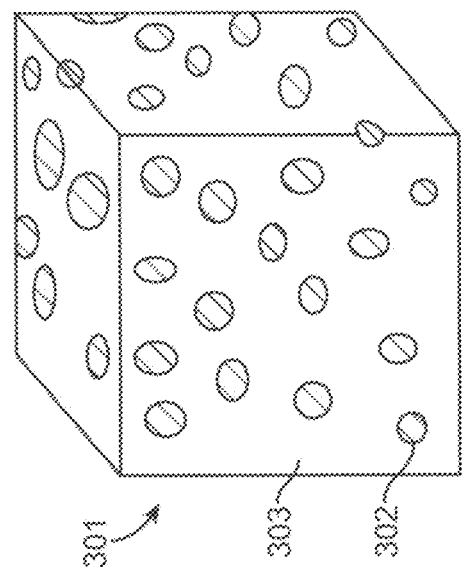

FIGS. 3a and 3b illustrate a section of a polymeric matrix having a morphology containing an agent-enriched phase at a concentration that is below about 30% by volume, and above about 30% by volume, respectively, according to some embodiments of the present invention. FIG. 3a illustrates a section of a polymeric matrix containing an agent-enriched phase at a concentration that is below about 30% by volume. The section 301 of the polymeric matrix is below the percolation threshold, since the agent-enriched phase 302 has not yet reached the concentration required to begin forming an interconnected network within the bulk phase 303 of the polymeric matrix. The "percolation threshold" is the point at which the agent-enriched phase begins to connect with itself and form an interconnected network of the agent-enriched phase within the polymeric matrix. The percolation threshold is the point at which the agent-enriched phase forms its own channel for diffusion.

FIG. 3b illustrates a section of a polymeric matrix containing an agent-enriched phase at a concentration that is above about 30% by volume. The section 304 of the polymeric matrix is above the percolation threshold, since the agent-enriched phase 305 has reached the concentration required to begin forming an interconnected network within the bulk phase 306 of the polymeric matrix.

In some embodiments, the morphology design can include control over the characteristics of the zone of phase separation between phases in a polymeric matrix, where the zone of phase separation can be thin, thick, continuous, non-continuous, hydrophobic, hydrophilic, porous, interconnected, dispersed, and the like. In some embodiments, the morphology can include, for example, other physical characteristics of a polymeric matrix including, but not limited to, the presence of pores, crystalline regions, amorphous regions, polymorphism of agents, the presence of metals, the presence of ceramics, and the like. The variations possible in the design of the morphology of a polymeric matrix can be extraordinarily large in number. The invention includes any polymeric matrix design that can be preselected and created to have an arrangement of components that provides a predictable performance characteristic.

The methods of the present invention include selecting a desired IM profile; forming a polymeric layer comprising the agent on a surface of the medical article; and subjecting the polymeric layer to a terminal process step to create the desired polymeric matrix. In most embodiments, the polymeric matrices may be selected to have a predetermined IM profile having at least a first component and a second component, where the first component can comprise a first polymer, and the second component can comprise an agent. In some embodiments, the second component can optionally comprise a second polymer.

In many embodiments, the morphology of the polymeric matrix can be selected to include a dispersed phase among the components of the matrix, and the dispersed phase may contain an agent. In some embodiments, the agent can be selected such that it dissolves in a polymer phase without a phase separation, or it can form a dispersed phase or a percolated phase. This dissolution can depend on factors including, but not limited to, the thermodynamic relationships between the agents and the polymers as well as the concentration of the agent in the polymeric matrix. One of skill will appreciate, for example, that the solubility parameters of the polymeric components of the matrix, as well as the miscibility of the combination of the polymers and agents, are design considerations that can assist in controlling the formation of phases in the polymeric matrix.

The polymeric matrix can be selected to include a morphology that includes a combination of polymers. In some embodiments, an agent can be selected that is more thermodynamically stable in a first polymer than in a second polymer, preferentially dissolve in the first polymer, and create a first polymer/agent combination as a dispersed phase that can be substantially or completely immiscible with the second polymer. In these embodiments, the second polymer can be referred to as a "bulk phase," and the first polymer/agent combination can be referred to as an "agent-enriched phase." The IM profile can refer to a morphology profile in any direction or combination of directions, or in any region or combination of regions, within a polymeric matrix. The emphasis of the present invention is that virtually any IM profile or combination of IM profiles can be preselected and created upon demand.

The predetermined IM profiles can be selected to provide a desired physical, mechanical, chemical, or biological characteristic of the polymeric matrix. Examples of physical characteristics include an increased or decreased water uptake, a dispersed-phase morphology, a percolated-phase morphology, a solid-solution morphology, and a porous morphology within the matrix. Examples of mechanical characteristics include an increased or decreased toughness, an increased elasticity, an increased or decreased Young's modulus, an increased tensile strength, and an increased tear strength of the matrix. Examples of chemical characteristics include an increased agent loading capacity, an increased durability, and an increased hydrophilicity of the matrix. Examples of biological characteristics include an increased biocompatibility, a desired bioactivity, an increased biobeneficiality, and a controllable rate of biodegradation and elimination of the matrix from a subject. Biobeneficiality is the attribute of a biobeneficial material which enhances the biocompatibility of the particles or device by being non-fouling, hemocompatible, actively non-thrombogenic, or antiinflammatory, all without depending on the release of a pharmaceutically active agent.

Water uptake by a polymeric matrix can be an important characteristic in the design of the matrix. Water can act as a plasticizer, diffusion medium, and can also hydrolyze chemical bonds within the matrix. Accordingly, control of water uptake can provide additional control over the mechanical properties of the matrix as well as the degradation rate, absorption rate, and the agent release rate of a medical article in vivo. In some embodiments, an increase in hydrolysis can also increase the in vivo release rate of an agent by creating channels within a medical article that can serve as transport pathways for diffusion of the agents from the composition within a subject. Moreover, water uptake can affect the storage life of a medical device by causing premature hydrolysis of the matrix, agent migration, and/or agent release.

The ability of the medical article to withstand stresses in vivo that can cause mechanical failure include, but are not limited to, cracking, flaking, peeling, fracturing, and perhaps a change in the modulus of the material that may affect, for example, the rigidity and toughness of the medical article. An example of a chemical property that can affect performance of a biodegradable composition in vivo is the rate of absorption of the composition by a subject. An example of a biological property that can affect performance of a composition in vivo is the bioactive and/or biobeneficial nature of the composition, both of which are described below.

It should be appreciated that the polymeric matrix can include other components, such as encapsulated agents that can be liposomally-encapsulated or polymer-encapsulated agents as part of the morphology; or a carrier, organic or inorganic, such as a porous calcium phosphate microparticle, where the carrier assists in obtaining a given loading of an agent needed for a localized treatment of a disease. Moreover, a polymeric matrix can comprise biodegradable components, and these components may be biodegradable due to the labile nature of chemical functionalities, such as ester groups between chemical moieties. Accordingly, the polymeric matrices can be designed to be biodegradable, such that they can be broken down, absorbed, resorbed and eliminated by a mammal.

In some embodiments, the polymeric matrix can release agents without biodegradation of the matrix, where the agent-release is at least partially independent of biodegradation. In other embodiments, the agents release during biodegradation of the matrix, such that the agent-release is at least partially dependent on biodegradation. In other examples, the polymeric matrix releases agents according to a combination of designs, wherein the combination can include agent release rates that are at least partially independent of, or at least partially dependent on, biodegradation of the polymeric matrix.

For the purposes of the present invention, a material is "biodegradable" when all or a portion of it is capable of being completely or substantially degraded or eroded when exposed to an in vivo environment or a representative in vitro environment. A polymer or polymeric matrix, for example, is capable of being degraded or eroded when it can be gradually broken-down, resorbed, absorbed and/or eliminated by, for example, hydrolysis, enzymolysis, oxidation, metabolic processes, bulk or surface erosion, and the like within a subject. It should be appreciated that traces or residue of polymer may remain on the device, near the site of the device, or near the site of a biodegradable device, following biodegradation. The terms "bioabsorbable" and "biodegradable" are used interchangeably in this application.

The methods of the present invention include forming a polymer layer comprising an agent on a surface of a medical article. In each of the embodiments, the term "layer" describes a thickness of a polymeric material within which an agent must pass through to be released into a subject. This term can refer, for example, to any individual polymeric material that may be used to form a medical device or a coating for a medical device. A layer can include, but is not limited to, polymeric material from a single-pass application or multiple-pass application, where a "pass" can be any single process step, or combination of steps, used to apply a material such as, for example, a pass of a spray coating device, a pass of an electrostatic coating device, a pass of a controlled-volume ejector, a dipping, an extrusion, a mold, a single dip in a layered manufacturing process, or a combination thereof. In general, a pass includes any single process step known to one of skill in the art that can be used to apply materials in the formation of a medical device or coating using a composition comprising a polymeric material. A layer can consist of a single pass or multiple passes. In some embodiments, the coating can be applied to an entire medical device or select regions of the medical device.

The term "thickness" of a layer can refer to the distance between opposite surfaces of a polymeric material that is used in the production of a medical device or coating. The thickness can refer to that of a single layer, a single layer within a combination of layers, or a combination layers. In some embodiments, the thickness of a polymeric material can be the thickness of a component within the structure of a medical device, such as, for example, the thickness of a strut within a stent. In other embodiments, the thickness of a polymeric material can be the thickness of a layer of coating applied to a medical device, such as a stent. In other embodiments, the thickness of a polymeric material can be the thickness of a combination of layers applied as a coating for a medical device.

In many embodiments, the thickness of a polymeric material can range from about 0.1 nm to about 1.0 cm, from about 0.1 nm to about 1.0 mm, from about 0.1 nm to about 100 µm, from about 0.1 nm to about 1 µm, from about 0.1 nm to about 100 nm, from about 0.1 nm to about 10 nm, from about 10 nm to about 100 nm, from about 10 µm to about 50 µm, from about 50 µm to about 100 µm, or any range therein. In other embodiments, the thickness of a polymeric matrix can range from about 1 µm to about 10 µm, which can be found, for example, in some of the current drug-eluting stent (DES) systems. In other embodiments, the thickness of the polymeric matrices can be regionally distributed throughout a device to create a variation in thicknesses such as, for example, the variation in thicknesses that can be found in an abluminally-coated DES stent.

The methods of forming a polymeric layer include, essentially, wet dispensing and dry dispensing, where the wet dispensing methods are dispensing a liquid. Wet dispensing methods can include, but are not limited to, spraying; dipping; constant volume applications such as, for example, a syringe pump; and constant pressure applications such as, for example, pneumatic dispensers. In some embodiments, the spraying can include, for example air atomization, ultrasound atomization, or a combination thereof. In some embodiments, the spray deposition can include, for example, direct deposition by acoustic ejection or piezoelectric droplet generation. In some embodiments, dipping can include lithographic techniques such as, for example, layered manufacturing.

Dry dispensing methods can include, but are not limited to, chemical vapor deposition (CVD) methods such as, for example, plasma deposition, and physical vapor deposition (PVD) methods such as, for example, ion-beam assisted deposition (IBAD). Other methods of dry deposition can include, for example, ink jet type depositions, which can include the deposition of charged particles.

In many embodiments, each layer can be applied to an implantable substrate by any method of dispensing a composition from any dispenser including, but not limited to, dipping, spraying, pouring, brushing, spin-coating, roller coating, meniscus coating, powder coating, inkjet-type application, controlled-volume application such as drop-on-demand, or a combination thereof. In these embodiments, a dry coating containing a biodegradable polymer may be formed on the stent when the solvent evaporates. In some embodiments, at least one of the layers can be formed on a stent by dissolving one or more biodegradable polymers, optionally with a non-biodegradable polymer, in one or more solvents, and either (i) spraying the solution on the stent or (ii) dipping the stent in the solution.

In other embodiments, a coating can be applied to a medical article, such as a stent, using methods that may include sputtering and gas-phase polymerization. Sputtering is a method that includes placing a polymeric material target in an environment that is conducive to applying energy to the polymeric material and sputtering the polymeric material from the target to the device to form a coating of the polymeric material on the device. Similarly, a gas-phase polymerization method includes applying energy to a monomer in the gas phase within an environment that is conducive to formation of a polymer from the monomer in the gas phase, and wherein the polymer formed coats the device.

The dispensing of the polymer layers may require the selection and use of solvents to assist in creating and using the compositions of the present invention. Since many applications of the present invention include "casting" of the compositions, the solvents will be referred to as "casting solvents." The casting solvent used to form polymer layers may be chosen based on several criteria including, for example, its polarity, ability to hydrogen bond, molecular size, volatility, biocompatibility, reactivity and purity. It is recognized that process conditions can affect the chemical structure of the underlying materials and, thus, affect their solubility in a casting solvent. It is also recognized that the kinetics of dissolution are a factor to consider when selecting a casting solvent, because a slow dissolution of an underlying material, for example, may not affect the performance characteristics of a product where the product is produced relatively quickly.

Exemplary casting solvents for use in the present invention include, but are not limited to, DMAC, DMF, THF, cyclohexanone, xylene, toluene, acetone, i-propanol, methyl ethyl ketone, propylene glycol monomethyl ether, methyl butyl ketone, ethyl acetate, n-butyl acetate, and dioxane. Solvent mixtures can be used as well. Representative examples of the mixtures include, but are not limited to, DMAC and methanol (50:50 w/w); water, i-propanol, and DMAC (10:3:87 w/w); i-propanol and DMAC (80:20, 50:50, or 20:80 w/w); acetone and cyclohexanone (80:20, 50:50, or 20:80 w/w); acetone and xylene (50:50 w/w); acetone, xylene and FLUX REMOVER AMS® (93.7% 3,3-dichloro-1,1,1,2,2-pentafluoropropane and 1,3-dichloro-1,1,2,2,3-pentafluoropropane, and the balance is methanol with trace amounts of nitromethane; Tech Spray, Inc.) (10:40:50 w/w); and 1,1,2-trichloroethane and chloroform (80:20 w/w).

The polymeric layer that is formed is subjected to a terminal process step to form the predetermined IM profiles of the present invention. The application of a terminal step can be used to change the arrangement of components within a polymeric matrix, for example, by promoting or inhibiting the migration of agents within a matrix; creating concentration profiles of agents within a matrix, promoting or inhibiting structural changes such as pores and channels within a matrix. A "terminal process step" is any step added subsequent to applying a polymeric material to a surface of a medical article, any step added subsequent to drying the polymeric material, any step added concurrent to applying the polymeric material to the surface of the medical article, any step added concurrent to the drying of the medical article, or any combination thereof. Examples of such steps are provided herein.

An agent that migrates with a solvent can be profiled by controlling the rate of solvent migration. The rate of solvent migration can be controlled, for example, by exposing the polymeric layer to a fluid while forming the layer, and by altering the pressure and/or temperature in the environment of a solvent removal process such as, for example, drying. Such control of the pressure and/or temperature can allow for indirect control of the initial morphology relative to position in a polymeric matrix. The IM profiles can then be designed to take on virtually any profile desired such as, for example, a predetermined wave profile that can provide a pulsed administration of a desired agent. Accordingly, in some embodiments, the terminal process step includes exposing the polymeric layer to a fluid while forming the layer, wherein the composition of the fluid is preselected to be miscible or immiscible with a component in the polymeric layer. The fluid phase can be a liquid phase, a gas phase, a combination thereof, or a phase consisting essentially of a gas phase.

In some embodiments, the gas phase contains water, where an increase or decrease in water concentration is referred to as an increase or decrease in humidity. In some embodiments, the gas phase is preferentially adsorbed by the agent. In some embodiments, the gas phase is preferentially adsorbed by one or more polymers in the polymeric matrix, wherein the polymer may or may not contain agent. In some embodiments, the solvents can be highly volatile solvents that are poor solvents such as, for example, Freon or a hydrocarbon. In some embodiments, the gas phase can selectively hydrolyze the polymeric matrix and/or create an intentional surface leaching or enrichment of an agent. In some embodiments, a liquid phase can selectively hydrolyze the polymeric matrix and/or create an intentional surface leaching or enrichment of an agent.

The surface energy relationship between the fluid phase and polymer layer can be a design parameter. The fluids miscibility with the polymer layer and its relative ability to wet or spread the polymer layer can control the effect of the fluid on the predetermined IM profile of the polymeric matrix. In some embodiments, the fluid phase is miscible with the polymer layer. In some embodiments, the fluid is polar, non-polar, or a combination thereof. In some embodiments, the fluid is hydrophilic, hydrophobic, amphiphilic, or a combination thereof. In some embodiments, the fluid comprises water to provide a desired humidity while forming the polymer layer. The fluid may also include a solvent used in forming the polymer layer.

In some embodiments, the terminal process step includes applying a pressure to the polymeric layer, or polymeric matrix formed from the layer, wherein the pressure can create a mechanical deformation in the polymer material. The pressure can be applied using any source of pressure known to one of skill in the art. In many embodiments, the pressure can be ambient pressure, a pressure higher than ambient pressure, a pressure lower than ambient pressure, or a variation in pressures that can include a pulsing of pressures. In some embodiments, the pressure can be isotropic or anisotropic. In these embodiments, the pressure can be a high isotropic pressure. In many embodiments, pressure can be applied to the polymer layer before the polymer layer is dried, after the polymer layer is dried, or a combination thereof. The pressure can be applied using any means known to one of skill in the art including, but not limited to a pressure vessel, or a mechanical pressure. Examples of a means for applying a mechanical pressure to a stent can be found in U.S. Pat. Nos. 6,510,722; 6,481,262; 6,277,110; 6,240,615; 6,202,272; 6,141,855; 6,125,523; 6,092,273; 6,082,990; 6,051,002; 6,024,737; 5,974,652; 5,972,016; 5,920,975; 5,893,852; 5,810,873; each of which is hereby incorporated herein by reference.

In some embodiments, the pressure can be a point source of pressure for localizing a desired IM profile in select areas to provide additional control over the rate of release of an agent from these select areas. This method of localizing the point source of pressure can also assist in providing a polymeric matrix having desired physical, mechanical, and chemical characteristics.

In some embodiments, the pressure can be applied at any time during the formation of a polymer layer as a negative pressure, and this pressure may also be pulsed during formation of the polymer layer to, for example, control the localization of agent across the thickness of the polymer layer so as to create a concentration profile. The concentration profile can be a constant, linear or non-linear to provide a rate of release that is tailored to a particular treatment design. Furthermore, the resulting polymeric matrix can be composed of multiple layers, wherein each layer can have any one or any combination of an independently formed concentration profile, an independently formed morphology profile, and an independently selected agent or agents to provide for a customized agent delivery.

In some embodiments, the pressure can be applied radially inward using a crimping device for collapsing an expandable stent onto a balloon catheter, a pressing device for pressing a collapsed stent onto a balloon catheter while heating the stent and the balloon catheter, or a combination thereof. In some embodiments, the pressure is applied only to an abluminal surface of a stent. In some embodiments, the pressure comprises pressure from inflation of the balloon on the balloon catheter. The pressure can range from about 10 psi to about 1000 psi, from about 50 psi to about 500 psi, from about 100 psi to about 300 psi, or any range therein.

In some embodiments, the pressure can be applied with an accompanying source of energy such as, for example, heat. In many embodiments, the energy can include, but is not limited to, heat, electromagnetic radiation, electron beam, ion or charged particle beam, neutral-atom beam, chemical energy, or a combination thereof. In some embodiments, the application of energy can result in a coating composition temperature that ranges from about 35° C. to about 100° C., from about 35° C. to about 80° C., from about 35° C. to about 55° C., or any range therein. In many embodiments, the temperature can be a temperature higher than ambient temperature, a temperature lower than ambient temperature, or a variation in temperatures that can include a pulsing of temperatures. In some embodiments, the pressure and temperature can be applied for a period of time ranging from about 1 second to about 3 minutes, from about 10 seconds to about 2 minutes, from about 15 seconds to about 90 seconds, from about 30 seconds to about 90 seconds, or any range therein.

Diffusion Coefficients

As described above, the release of the agent from a medical article will most often include a diffusion parameter, such that the design of a polymeric matrix can include diffusion considerations in obtaining control over the release of the agent. The process of diffusion of an agent from a polymeric matrix in the form of a coating can be affected by the following four controllable factors: (1) coating parameters, (2) coating process, (3) polymer physicochemical properties, and (4) agent physicochemical properties.

The coating parameters can include, but are not limited to, the initial solid phase concentration distribution, which includes the drug to polymer (D/P) ratio, the thickness of an agent-free polymer top-coating, the total drug content, the dispersed phase microstructure, and the like. The coating process can include, but is not limited to, the selection of solvents, the thermal history of processing, the thermodynamics of phase separation, the solution thermodynamics, and kinetics, to name a few. Polymer physicochemical properties can include, but are not limited to, glass transition temperature (Tg), melting temperature (Tm), heat of fusion ($\Delta H_f$), percent crystallinity, water absorption, lipid-induced swelling, and the like. Agent physicochemical properties include, but are not limited to, the degree and type of dispersed phase parameters, the extent of solid solution, and the polymorphism of the agent (e.g. different crystalline forms of a drug).

The diffusion coefficient that is measured across a polymer matrix having multiple components can be described as an "effective-diffusion coefficient." This is because the effective-diffusion coefficient depends, at least in part, on the often complex morphology of the polymer matrix within which the agent passes. Without intending to be bound by any theory or mechanism of action, the effective-diffusion coefficient can be divided into at least two modes that can be referred to as "biphasic modes:"

(1) in a first mode, the effective diffusivity corresponds to the transport of an agent dissolved in a polymeric matrix without phase separation; or, an agent that primarily transports out of a dispersed agent phase into a surrounding polymeric matrix and then diffuses out of the surrounding polymeric matrix; and, (2) in a second mode, the effective diffusivity corresponds to the transport of an agent through a dispersed agent phase, for example, a dispersed agent phase within a polymeric matrix that has interconnected to create a closely connected network (i.e. a "percolated" phase) by virtue of being densely distributed throughout the polymeric matrix; accordingly, the effective diffusivity can include an intrinsic diffusivity of the agent through a water medium in the polymeric matrix in addition to the tortuosity and porosity of a percolated-phase passage that has formed throughout the polymeric matrix.

In some embodiments, the overall mass transport can be considered as dependent on one or a combination of the biphasic modes. Since the diffusion coefficient can be proportional to the rate of release, it can be measured experimentally for each polymeric matrix and used as a defining characteristic for the release of a particular agent from that system. Using this methodology, one of skill can characterize polymeric matrices and design predetermined IM profiles that are known to provide an agent release that, although may be variable in rate over the life of a medical article, is relatively controllable and predictable.

The creation of an interconnected agent-enriched dispersed phase morphology provides a means for controlling the diffusion coefficient. In many embodiments, an agent-enriched phase will reach a percolation threshold at a concentration of about 30% by volume within the combined volume of the polymer matrix and agent. In some embodiments, diffusion of an agent through an interconnected, agent-rich dispersed phase can result in either a faster or slower release of an agent, and the result depends on the relationship between the agent and the agent-enriched phase. In some embodiments, the agent exists in both the interconnected, agent-enriched dispersed phase and the bulk phase, such that release of the agent occurs through diffusion across both phases. In some embodiments, the agent has to diffuse through the phase boundary between the dispersed phase and the bulk phase, and the amount and characteristics of the phase boundary can affect the rate of release of the agent.

Effects of IM Profiles on Physical and Mechanical Properties

Designing predetermined IM profiles of the agents within the polymeric matrices can assist in obtaining and maintaining desirable physical and mechanical properties and, thus, aid in preventing structural failure within medical articles. Many medical implants, such as stents, can undergo a great deal of strain and stress during their manufacture and use which can result in structural failure. Structural failure can occur, for example, as a result of manipulating an implant in preparation for placing the implant in a subject and while placing the implant in a desired location in a subject. As a result, the ability to identify desirable polymeric matrices with morphologies that can withstand such stress and strain can be invaluable to the success of a medical procedure.

Figure 4:
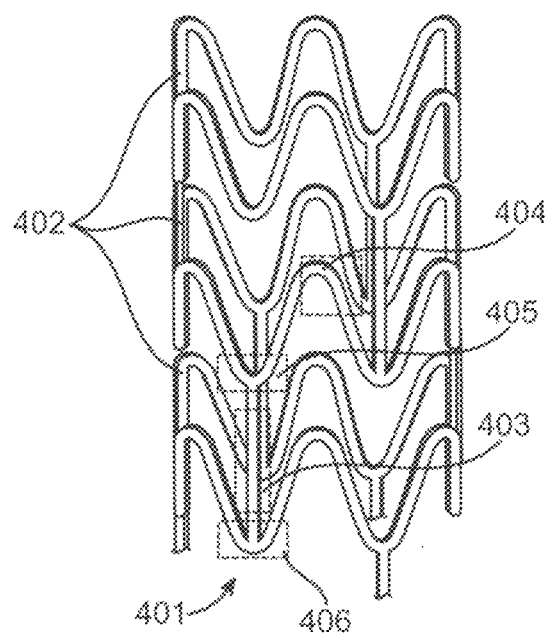
FIG. 4 illustrates an example of a three-dimensional view of a stent according to some embodiments of the present invention.

A stent is an example of an implant that can undergo a great deal of physical and mechanical stress. A stent may be compressed, inserted into a small vessel through a catheter, and then expanded to a larger diameter in a subject. FIG. 4 illustrates an example of a three-dimensional view of a stent according to some embodiments of the present invention. The stent 401 may be made up of a pattern of a number of interconnecting structural elements or struts 402. As described herein, the embodiments disclosed are not limited to stents or to the stent pattern illustrated in FIG. 4 and are easily applicable to other patterns and other devices. The variations in the structure of patterns are virtually unlimited. Controlled application of particular agents in low strain areas 403 and high strain areas 404, 405, and 406 of a stent, for example, can help to avoid problems, such as cracking and flaking, that can occur during implantation of the stent. Controlled application of the agents can also be obtained through control of the morphology of a polymeric matrix that forms after the application.

The Polymers

The polymers used in the present invention may include, but are not limited to, condensation polymers and copolymers, and should be chosen according to a desired performance parameter of a product that will be formed from the composition. Such performance parameters may include, for example, the toughness of a medical article, the capacity for the loading concentration of an agent, and the rate of biodegradation and elimination of the composition from a subject. If the other polymers in a composition are non-biodegradable, they should be sized to produce polymer fragments that can clear from the subject following biodegradation of the composition.

In most embodiments, the polymers that can be used include natural or synthetic polymers; homopolymers and copolymers, such as, for example, copolymers that are random, alternating, block, graft, and/or crosslinked; or any combination and/or blend thereof. The copolymers include polymers with more than two different types of repeating units such as, for example, terpolymers. In some embodiments, the polymers can be considered more hydrophobic in character such as, for example, poly(D,L-lactide), poly(caprolactone), and poly(vinylidene fluoride-co-hexafluoro-propylene) (Solef®). In some embodiments, the polymers can be considered more hydrophilic in character such as, for example, copolymers containing poly(ethylene glycol) (PEG). In these embodiments, the copolymers can include, but are not limited to, copolymers of poly(butylene terephthalate) and poly(ethylene glycol) (PBT-PEG; PolyActive®), a poly(hydroxyalkanoate) and PEG (PHA-PEG), a poly(ester amide) and PEG (PEA-PEG), or poly(butyl methacrylate) and PEG (PBMA-PEG). One of skill in the art will be familiar with the wide variety of polymers that are considered as hydrophilic, such as the many functionalized hydrophobic polymers that are known—the present invention encompasses the entirety of these polymers.

Examples of other polymers that can be used in the present invention include, but are not limited to, poly(acrylates) such as poly(butyl methacrylate), poly(ethyl methacrylate), poly(hydroxyethyl methacrylate), poly(ethyl methacrylate-co-butyl methacrylate), copolymers of ethylene-methyl methacrylate; poly (2-acrylamido-2-methylpropane sulfonic acid), and polymers and copolymers of aminopropyl methacrylamide; poly(cyanoacrylates); poly(carboxylic acids); poly(vinyl alcohols); poly(maleic anhydride) and copolymers of maleic anhydride; fluorinated polymers or copolymers such as poly(vinylidene fluoride), poly(vinylidene fluoride-co-hexafluoro propene), poly(tetrafluoroethylene), and expanded poly(tetrafluoroethylene); poly(sulfone); poly(N-vinyl pyrrolidone); poly(aminocarbonates); poly(iminocarbonates); poly(anhydride-co-imides), poly(hydroxyvalerate); poly(L-lactic acid); poly(L-lactide); poly(caprolactones); poly(lactide-co-glycolide); poly(hydroxybutyrates); poly(hydroxybutyrate-co-valerate); poly(dioxanones); poly(orthoesters); poly(anhydrides); poly(glycolic acid); poly(glycolide); poly(D,L-lactic acid); poly(D,L-lactide); poly(glycolic acid-co-trimethylene carbonate); poly(phosphoesters); poly(phosphoester urethane); poly(trimethylene carbonate); poly(iminocarbonate); poly(ethylene); poly(propylene) co-poly(ether-esters) such as, for example, poly(dioxanone) and poly(ethylene oxide)/poly(lactic acid); poly(anhydrides), poly(alkylene oxalates); poly(phosphazenes); poly(urethanes); silicones; poly(esters; poly(olefins); copolymers of poly(isobutylene); copolymers of ethylene-alphaolefin; vinyl halide polymers and copolymers such as poly(vinyl chloride); poly(vinyl ethers) such as poly(vinyl methyl ether); poly(vinylidene halides) such as, for example, poly(vinylidene chloride); poly(acrylonitrile); poly(vinyl ketones); poly(vinyl aromatics) such as poly(styrene); poly(vinyl esters) such as poly(vinyl acetate); copolymers of vinyl monomers and olefins such as poly(ethylene-co-vinyl alcohol) (EVAL), copolymers of acrylonitrile-styrene, ABS resins, and copolymers of ethylene-vinyl acetate; poly(amides) such as Nylon 66 and poly(caprolactam); alkyd resins; poly(carbonates); poly(oxymethylenes); poly(imides); poly(ester amides); poly(ethers) including poly(alkylene glycols) such as, for example, poly(ethylene glycol) and poly(propylene glycol); epoxy resins; polyurethanes; rayon; rayon-triacetate; biomolecules such as, for example, fibrin, fibrinogen, starch, poly(amino acids); peptides, proteins, gelatin, chondroitin sulfate, dermatan sulfate (a copolymer of D-glucuronic acid or L-iduronic acid and N-acetyl-D-galactosamine), collagen, hyaluronic acid, and glycosaminoglycans; other polysaccharides such as, for example, poly(N-acetylglucosamine), chitin, chitosan, cellulose, cellulose acetate, cellulose butyrate, cellulose acetate butyrate, cellophane, cellulose nitrate, cellulose propionate, cellulose ethers, and carboxymethylcellulose; and derivatives, analogs, homologues, congeners, salts, copolymers and combinations thereof. In some embodiments, the polymers are selected such that they specifically exclude any one or any combination of these polymers.

Examples of biodegradable polymers include, but are not limited to, polymers having repeating units such as, for example, an α-hydroxycarboxylic acid, a cyclic diester of an α-hydroxycarboxylic acid, a dioxanone, a lactone, a cyclic carbonate, a cyclic oxalate, an epoxide, a glycol, an anhydride, a lactic acid, a glycolic acid, a lactide, a glycolide, an ethylene oxide, an ethylene glycol, or combinations thereof. In other embodiments, the biodegradable polymers include, but are not limited to, polyesters, poly(ester amides); poly(hydroxyalkanoates) (PHA), amino acids; PEG and/or alcohol groups, polycaprolactones, poly(D-lactide), poly(L-lactide), poly(D,L-lactide), poly(meso-lactide), poly(L-lactide-co-meso-lactide), poly(D-lactide-co-meso-lactide), poly(D,L-lactide-co-meso-lactide), poly(D,L-lactide-co-PEG) block copolymers, poly(D,L-lactide-co-trimethylene carbonate), polyglycolides, poly(lactide-co-glycolide), polydioxanones, polyorthoesters, polyanhydrides, poly(glycolic acid-co-trimethylene carbonate), polyphosphoesters, polyphosphoester urethanes, poly(amino acids), polycyanoacrylates, poly(trimethylene carbonate), poly(imino carbonate), polycarbonates, polyurethanes, copoly(ether-esters) (e.g. PEO/PLA), polyalkylene oxalates, polyphosphazenes, PHA-PEG, and any derivatives, analogs, homologues, salts, copolymers and combinations thereof.

In some embodiments, the polymers can be poly(glycerol sebacate); tyrosine-derived polycarbonates containing desaminotyrosyl-tyrosine alkyl esters such as, for example, desaminotyrosyl-tyrosine ethyl ester (poly(DTE carbonate)); and any derivatives, analogs, homologues, salts, copolymers and combinations thereof. In some embodiments, the polymers are selected such that they specifically exclude any one or any combination of any of the polymers taught herein.

Polymers that degrade should be designed to form fragments that can be absorbed by the subject undergoing treatment. In some embodiments, the number average molecular weight of the polymer fragments should be at or below about 40,000 Daltons, or any range therein. In other embodiments, the molecular weight of the fragments range from about 300 Daltons to about 40,000 Daltons, from about 8,000 Daltons to about 30,000 Daltons, from about 10,000 Daltons to about 20,000 Daltons, or any range therein. The molecular weights are taught herein as a number average molecular weight.

The Agents

An "agent" can include any chemical moiety having a characteristic that is bioactive, biobeneficial, diagnostic, plasticizing, or a combination of these characteristics, when used in the present invention. A "moiety" can include any chemical entity composed of as little as a single atom, a small molecule, a peptide, a protein, an oligonucleotide, a polynucleotide, a functional group, a bonded residue in a macromolecule, an individual unit in a copolymer, or an entire polymeric block, to name a few. A "bioactive agent" is a moiety that can be combined with a polymer and provides a therapeutic effect, a prophylactic effect, both a therapeutic and a prophylactic effect, or other biologically active effect within a subject. Moreover, the bioactive agents of the present invention may remain linked to a portion of the polymer or be released from the polymer. A "biobeneficial agent" is an agent that can be combined with a polymer and provide a biological benefit within a subject without necessarily being released from the polymer. The agent may comprise phosphorylcholine.

A "diagnostic agent" is a type of bioactive agent that can be used, for example, in diagnosing the presence, nature, or extent of a disease or medical condition in a subject. In one embodiment, a diagnostic agent can be any agent that may be used in connection with methods for imaging an internal region of a patient and/or diagnosing the presence or absence of a disease in a patient. Diagnostic agents include, for example, contrast agents for use in connection with ultrasound imaging, magnetic resonance imaging (MRI), nuclear magnetic resonance (NMR), computed tomography (CT), electron spin resonance (ESR), nuclear medical imaging, optical imaging, elastography, and radiofrequency (RF) and microwave lasers. Diagnostic agents may also include any other agents useful in facilitating diagnosis of a disease or other condition in a patient, whether or not imaging methodology is employed.

The terms "plasticizer" and "plasticizing agent" can be used interchangeably in the present invention, and can refer to any agent, including any agent described above, where the agent can be used to modify the mechanical properties of the polymeric material. Plasticizers can, for example, reduce crystallinity, lower the glass-transition temperature ($T_g$), or reduce the intermolecular forces between polymers and enhance mobility between polymers. The mechanical properties that are modified include, but are not limited to, Young's modulus, impact resistance (toughness), tensile strength, and tear strength.

The bioactive agents can be any moiety capable of contributing to a therapeutic effect, a prophylactic effect, both a therapeutic and prophylactic effect, or other biologically active effect in a mammal. The agent can also have diagnostic properties. The bioactive agents include, but are not limited to, small molecules, nucleotides, oligonucleotides, polynucleotides, amino acids, oligopeptides, polypeptides, and proteins. In one example, the bioactive agent inhibits the activity of vascular smooth muscle cells. In another example, the bioactive agent controls migration or proliferation of smooth muscle cells to inhibit restenosis.

Bioactive agents include, but are not limited to, antiproliferatives, antineoplastics, antimitotics, anti-inflammatories, antiplatelets, anticoagulants, antifibrins, antithrombins, antibiotics, antiallergics, antioxidants, and any prodrugs, metabolites, analogs, homologues, congeners, derivatives, salts and combinations thereof. It is to be appreciated that one skilled in the art should recognize that some of the groups, subgroups, and individual bioactive agents may not be used in some embodiments of the present invention.

Antiproliferatives include, for example, actinomycin D, actinomycin IV, actinomycin actinomycin $X_1$, actinomycin $C_1$, dactinomycin (COSMEGEN®, Merck & Co., Inc.), imatinib mesylate, and any prodrugs, metabolites, analogs, homologues, congeners, derivatives, salts and combinations thereof. Antineoplastics or antimitotics include, for example, paclitaxel (TAXOL®, Bristol-Myers Squibb Co.), docetaxel (TAXOTERE®, Aventis S.A.), midostaurin, methotrexate, azathioprine, vincristine, vinblastine, fluorouracil, doxorubicin hydrochloride (ADRIAMYCIN®, Pfizer, Inc.) and mitomycin (MUTAMYCIN®, Bristol-Myers Squibb Co.), midostaurin, and any prodrugs, metabolites, analogs, homologues, congeners, derivatives, salts and combinations thereof.

Antiplatelets, anticoagulants, antifibrin, and antithrombins include, for example, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors (ANGIOMAX®, Biogen, Inc.), and any prodrugs, metabolites, analogs, homologues, congeners, derivatives, salts and combinations thereof.

Cytostatic or antiproliferative agents include, for example, angiopeptin, angiotensin converting enzyme inhibitors such as captopril (CAPOTEN® and CAPOZIDE®, Bristol-Myers Squibb Co.), cilazapril or lisinopril (PRINIVIL® and PRINZIDE®, Merck & Co., Inc.); calcium channel blockers such as nifedipine; colchicines; fibroblast growth factor (FGF) antagonists, fish oil (omega 3-fatty acid); histamine antagonists; lovastatin (MEVACOR®, Merck & Co., Inc.); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide; imatinib mesylate; and any prodrugs, metabolites, analogs, homologues, congeners, derivatives, salts and combinations thereof. Antiallergic agents include, but are not limited to, pemirolast potassium (ALAMAST®, Santen, Inc.), and any prodrugs, metabolites, analogs, homologues, congeners, derivatives, salts and combinations thereof.

Other bioactive agents useful in the present invention include, but are not limited to, free radical scavengers; nitric oxide donors; rapamycin; methyl rapamycin; 42-Epi-(tetrazoylyl)rapamycin (ABT-578); 40-O-(2-hydroxy)ethyl-rapamycin (everolimus); tacrolimus; pimecrolimus; 40-O-(3-hydroxy)propyl-rapamycin; 40-O-[2-(2-hydroxy)ethoxy]ethyl-rapamycin; tetrazole containing rapamycin analogs such as those described in U.S. Pat. No. 6,329,386; estradiol; clobetasol; idoxifen; tazarotene; alpha-interferon; host cells such as epithelial cells; genetically engineered epithelial cells; dexamethasone; and, any prodrugs, metabolites, analogs, homologues, congeners, derivatives, salts and combinations thereof.

Free radical scavengers include, but are not limited to, 2,2',6,6'-tetramethyl-1-piperinyloxy, free radical (TEMPO); 4-amino-2,2',6,6'-tetramethyl-1-piperinyloxy, free radical (4-amino-TEMPO); 4-hydroxy-2,2',6,6'-tetramethyl-piperidene-1-oxy, free radical (TEMPOL), 2,2',3,4,5,5'-hexamethyl-3-imidazolinium-1-yloxy methyl sulfate, free radical; 16-doxyl-stearic acid, free radical; superoxide dismutase mimic (SODm) and any analogs, homologues, congeners, derivatives, salts and combinations thereof. Nitric oxide donors include, but are not limited to, S-nitrosothiols, nitrites, N-oxo-N-nitrosamines, substrates of nitric oxide synthase, diazenium diolates such as spermine diazenium diolate and any analogs, homologues, congeners, derivatives, salts and combinations thereof.

A biological benefit may be that the polymer or polymeric matrix becomes non-thrombogenic, such that protein absorption is inhibited or prevented to avoid formation of a thromboembolism; promotes healing, such that endothelialization within a blood vessel is not exuberant but rather forms a healthy and functional endothelial layer; or is non-inflammatory, such that the biobeneficial agent acts as a biomimic to passively avoid attracting monocytes and neutrophils, which could lead to an event or cascade of events that create inflammation.

Examples of biobeneficial agents include, but are not limited to, carboxymethylcellulose; poly(alkylene glycols) such as, for example, PEG; poly(N-vinyl pyrrolidone); poly (acrylamide methyl propane sulfonic acid); poly(styrene sulfonate); sulfonated polysaccharides such as, for example, sulfonated dextran; sulfated polysaccharides such as, for example, sulfated dextran and dermatan sulfate; and glycosaminoglycans such as, for example, hyaluronic acid and heparin; and any derivatives, analogs, homologues, congeners, salts, copolymers and combinations thereof. In some embodiments, the biobeneficial agents can be prohealing such as, for example, poly(ester amides), elastin, silk-elastin, collagen, atrial natriuretic peptide (ANP); and peptide sequences such as, for example, those comprising Arg-Gly-Asp (RGD). In other embodiments, the biobeneficial agents can be non-thrombotics such as, for example, thrombomodulin; and antimicrobials such as, for example, the organosilanes. It is to be appreciated that one skilled in the art should recognize that some of the groups, subgroups, and individual biobeneficial agents may not be used in some embodiments of the present invention.

Examples of heparin derivatives include, but are not limited to, earth metal salts of heparin such as, for example, sodium heparin, potassium heparin, lithium heparin, calcium heparin, magnesium heparin, and low molecular weight heparin. Other examples of heparin derivatives include, but are not limited to, heparin sulfate, heparinoids, heparin-based compounds and heparin derivatized with hydrophobic materials.

Examples of hyaluronic acid derivatives include, but are not limited to, sulfated hyaluronic acid such as, for example, O-sulphated or N-sulphated derivatives; esters of hyaluronic acid wherein the esters can be aliphatic, aromatic, arylaliphatic, cycloaliphatic, heterocyclic or a combination thereof; crosslinked esters of hyaluronic acid wherein the crosslinks can be formed with hydroxyl groups of a polysaccharide chain; crosslinked esters of hyaluronic acid wherein the crosslinks can be formed with polyalcohols that are aliphatic, aromatic, arylaliphatic, cycloaliphatic, heterocyclic, or a combination thereof; hemiesters of succinic acid or heavy metal salts thereof; quaternary ammonium salts of hyaluronic acid or derivatives such as, for example, the O-sulphated or N-sulphated derivatives.

Examples of poly(alkylene glycols) include, but are not limited to, PEG, mPEG, poly(ethylene oxide), polypropylene glycol)(PPG), poly(tetramethylene glycol), and any derivatives, analogs, homologues, congeners, salts, copolymers and combinations thereof. In some embodiments, the poly(alkylene glycol) is PEG. In other embodiments, the poly(alkylene glycol) is mPEG. In some embodiments, the poly(alkylene glycol) is poly(ethylene glycol-co-hydroxybutyrate).

The copolymers that may be used as biobeneficial agents include, but are not limited to, any derivatives, analogs, homologues, congeners, salts, copolymers and combinations of the foregoing examples of agents. Examples of copolymers that may be used as biobeneficial agents in the present invention include, but are not limited to, dermatan sulfate, which is a copolymer of D-glucuronic acid or L-iduronic acid and N-acetyl-D-galactosamine; poly(ethylene oxide-co-propylene oxide); copolymers of PEG and hyaluronic acid; copolymers of PEG and heparin; copolymers of PEG and hirudin; graft copolymers of poly(L-lysine) and PEG; copolymers of PEG and a poly(hydroxyalkanoate) such as, for example, poly(ethylene glycol-co-hydroxybutyrate); and, any derivatives, analogs, congeners, salts, or combinations thereof. In some embodiments, the copolymer that may be used as a biobeneficial agent can be a copolymer of PEG and hyaluronic acid, a copolymer of PEG and hirudin, and any derivative, analog, congener, salt, copolymer or combination thereof. In some embodiments, the copolymer that may be used as a biobeneficial agent is a copolymer of PEG and a poly(hydroxyalkanoate) such as, for example, poly (hydroxybutyrate); and any derivative, analog, congener, salt, copolymer or combination thereof.

Examples of diagnostic agents include radiopaque materials and include, but are not limited to, materials comprising iodine or iodine-derivatives such as, for example, iohexal and iopamidol, which are detectable by x-rays. Other diagnostic agents such as, for example, radioisotopes, are detectable by tracing radioactive emissions. Other diagnostic agents may include those that are detectable by magnetic resonance imaging (MRI), ultrasound and other imaging procedures such as, for example, fluorescence and positron emission tomagraphy (PET). Examples of agents detectable by MRI are paramagnetic agents, which include, but are not limited to, gadolinium chelated compounds. Examples of agents detectable by ultrasound include, but are not limited to, perflexane. Examples of fluorescence agents include, but are not limited to, indocyanine green. Examples of agents used in diagnostic PET include, but are not limited to, fluorodeoxyglucose, sodium fluoride, methionine, choline, deoxyglucose, butanol, raclopride, spiperone, bromospiperone, carfentanil, and flumazenil.

In some embodiments, a combination of agents can be applied, as taught herein, within a medical device, on a medical device, or positioned within a controlled volume at a predetermined region on the device or within a coating on the device. In some embodiments, the agent combination includes everolimus and clobetasol. In other embodiments, the agent combination includes tacrolimus and rapamycin. In other embodiments, the agent combination includes tacrolimus and everolimus. In other embodiments, the agent combination can include rapamycin and paclitaxel. In other embodiments, the agent combination can include an anti-inflammatory such as, for example, a corticosteroid and an antiproliferative such as, for example, everolimus. In some embodiments, the agent combinations can provide synergistic effects for preventing or inhibiting conditions such as, for example, restenosis, atherosclerosis, vulnerable plaque, diffuse coronary artery disease, and the like, that may be prevented, inhibited, mitigated, or otherwise treated, using an agent-eluting stent.

Examples of plasticizing agents include, but are not limited to, low molecular weight polymers such as, for example, single-block polymers, multi-block copolymers, and other copolymers such as graft copolymers; oligomers such as ethyl-terminated oligomers of lactic acid; small organic molecules; hydrogen bond forming organic compounds with and without hydroxyl groups; polyols such as low molecular weight polyols having aliphatic hydroxyls; alkanols such as butanols, pentanols and hexanols; sugar alcohols and anhydrides of sugar alcohols; polyethers such as poly(alkylene glycols); esters such as citrates, phthalates, sebacates and adipates; polyesters; aliphatic acids; proteins such as animal proteins and vegetable proteins; oils such as, for example, the vegetable oils and animal oils; silicones; acetylated monoglycerides; amides; acetamides; sulfoxides; sulfones; pyrrolidones; oxa acids; diglycolic acids; and any analogs, derivatives, copolymers and combinations thereof.

The amount of plasticizer used in the present invention, can range from about 0.001% to about 70%; from about 0.01% to about 60%; from about 0.1% to about 50%; from about 0.1% to about 40%; from about 0.1% to about 30%; from about 0.1% to about 25%; from about 0.1% to about 20%; from about 0.1% to about 10%; from about 0.4% to about 40%; from about 0.6% to about 30%; from about 0.75% to about 25%; from about 1.0% to about 20%; and any range therein, as a weight percentage based on the total weight of the polymer and agent or combination of agents. The plasticizers can be combined to obtain the desired function. In some embodiments, a secondary plasticizer is combined with a primary plasticizer in an amount that ranges from about 0.001% to about 20%; from about 0.01% to about 15%; from about 0.05% to about 10%; from about 0.75% to about 7.5%; from about 1.0% to about 5%, or any range therein, as a weight percentage based on the total weight of the polymer any agent or combination of agents.

It should be appreciated that classification of an agent as a biobeneficial agent does not preclude the use of that agent as a bioactive agent, diagnostic agent and/or plasticizing agent. Likewise, classification of an agent as a bioactive agent does not preclude the use of that agent as a diagnostic agent, biobeneficial agent and/or plasticizing agent. Furthermore, classification of an agent as a plasticizing agent does not preclude the use of that agent as a biobeneficial agent, bioactive agent, and/or diagnostic agent.

Agents that are released into the body of the subject being treated should be sized such that the subject can absorb the agent. In some embodiments, the molecular weight of an agent should be at or below about 40,000 Daltons, or any range therein, to ensure elimination of the agent from a mammal. In one embodiment, the molecular weight of the agent ranges from about 300 Daltons to about 40,000 Daltons, from about 8,000 Daltons to about 30,000 Daltons, from about 10,000 Daltons to about 20,000 Daltons, or any range therein. If upon release, the biobeneficial agent is rapidly broken down in the body, then the molecular weight of the agent could be greater than about 40,000 Daltons without compromising patient safety. The molecular weights as taught herein are a number average molecular weight.

The characteristics of the agents and the manner in which they are incorporated into a polymeric matrix can affect the IM profile and agent release. In some embodiments, the agents can be chemically connected to a polymer by covalent bonds; chemically connected to a polymer by non-covalent bonds such as, for example, by ionic bonds or inter-molecular attractions; physically connected to a polymer; or a combination thereof. In some embodiments, the agents can be chemically and physically connected with a polymer.

Examples of ionic bonding can include, but are not limited to, ionic bonding of an anionic site to a cationic site between polymers. In some embodiments, an anionic site can be bound to a quaternary amine. Examples of inter-molecular attractions include, but are not limited to, hydrogen bonding such as, for example, the permanent dipole interactions between hydroxyl, amino, carboxyl, amide, and sulfhydryl groups, and combinations thereof. Examples of physical connections can include, but are not limited to, interpenetrating networks and chain entanglement. The polymers can also be blended or mixed with the agents.

In some embodiments, the agents have a reactive group that can be used to link the agents to the polymer. Examples of reactive groups include, but are not limited to, hydroxyl, acyl, amino, amido, carbonyl, carboxyl, and sulfhydryl groups. In some embodiments, the agents can be released or can separate from the polymer composition. In some embodiments, the agents can be linked to the medical article through linkages that are designed to provide preselected release rates of the agent from the medical article. In these embodiments, the agent may be linked to the medical article through ether, amide, ester, orthoester, anhydride, ketal, acetal, carbonate, and all-aromatic carbonate linkages to provide, for example, a desired rate of hydrolysis of the agent from the medical article.

The selection of a desired release rate of an agent can depend on a variety of factors such as, for example, the therapeutic, prophylactic, ameliorative or diagnostic needs of a patient. In some embodiments, the agent can comprise an antiproliferative and should have a sustained release ranging from about 1 week to about 10 weeks, from about 2 weeks to about 8 weeks, from about 3 weeks to about 7 weeks, from about 4 weeks to about 6 weeks, and any range therein. In some embodiments, the agent can comprise an anti-inflammatory and should have a sustained release ranging from about 6 hours to about 3 weeks, from about 12 hours to about 2 weeks, from about 18 hours to about 10 days, from about 1 day to about 7 days, from about 2 days to about 6 days, or any range therein. In general, any release rate can be desired and can be a variable rate in some embodiments, however, the release should range from about 4 hours to about 12 weeks; alternatively, from about 6 hours to about 10 weeks; or from about 1 day to about 8 weeks. Since the agents of the present invention can be added in combination to obtain desired effects, one of skill in the art can tailor the compositions to release each agent of interest in the desired amounts.

The amounts of the agents that compose the polymeric compositions vary according to a variety of factors including, but not limited to, the biological activity of the agent; the age, body weight, response, or the past medical history of the subject; the type of disease such as, for example, atherosclerotic disease; the presence of systemic diseases such as, for example, diabetes; the pharmacokinetic and pharmacodynamic effects of the agents or combination of agents; and the design of the compositions for sustained release of the agents. Factors such as these are routinely considered by one of skill in the art when administering an agent to a subject. Effective amounts, for example, may be extrapolated from in vitro or animal model systems. In some embodiments, the agent or combination of agents have a concentration that ranges from about 0.001% to about 75%; from about 0.01% to about 70%; from about 0.1% to about 60%; from about 0.25% to about 60%; from about 0.5% to about 50%; from about 0.75% to about 40%; from about 1.0% to about 30%; from about 2% to about 20%; and, any range therein, where the percentage is based on the total weight of the polymer and agent or combination of agents.

Other Components and Characteristics

The polymeric matrices can also include polymers combined with ceramics and/or metals. Examples of ceramics include, but are not limited to, hydroxyapatite, BIOGLASS®, and absorbable glass. Examples of metals include, but are not limited to magnesium, copper, titanium, and tantalum. In some embodiments, a polymeric matrix may be formed using a pore forming agent. The pore forming agent can be dispersed or mixed within the composition used to form the polymeric layer. One of skill will appreciate that porous structure of the polymeric matrix may influence the degradation rate. Such properties include, but are not limited to, pore size distribution and porosity. Porosity may be defined as the ratio of the void volume to the total volume of the polymeric matrix. In some embodiments, the erosion profile may be controlled by controlling the pore size distribution and porosity of the polymeric matrix.

Potential Coating Configurations

There are many coating configurations within the scope of the present invention, and each configuration can include any number and combination of layers. In some embodiments, the coatings of the present invention can comprise one or a combination of the following four types of layers:

(a) an agent layer, which may comprise a polymer and an agent or, alternatively, a polymer free agent;

(b) an optional primer layer, which may improve adhesion of subsequent layers on the implantable substrate or on a previously formed layer;

(c) an optional topcoat layer, which may serve as a way of controlling the rate of release of an agent; and (d) an optional biocompatible finishing layer, which may improve the biocompatibility of the coating.

In some embodiments, a pure agent can be applied directly to at least a part of an implantable substrate as a layer to serve as a reservoir for at least one bioactive agent. In another embodiment, the agent can be combined with a polymer. In another embodiment, an optional primer layer can be applied between the implantable substrate and the agent layer to improve adhesion of the agent layer to the implantable substrate and can optionally comprise an agent.

In other embodiments, a pure agent layer can be sandwiched between layers comprising biodegradable polymer. In other embodiments, the optional topcoat layer can be applied over at least a portion of the agent layer to serve as a topcoat to assist in the control the rate of release of agents and can optionally comprise an agent. In another embodiment, a biocompatible finishing layer can be applied to increase the biocompatibility of the coating by, for example, increasing acute hemocompatibility, and this layer can also comprise an agent.

In some embodiments, the topcoat layer and the biocompatible finishing layer can be comprised of the same components, different components, or share a combination of their components. In some embodiments, the topcoat layer and the biocompatible finishing layer can be the same layer, different layers, or can be combined. In most embodiments, the finishing layer can be more biocompatible than the topcoat layer.

In some embodiments, the methods of the present invention can be used to coat a medical device with layers formed from polymeric matrices having more than one coating configuration. In some embodiments, the coating configurations can include a pure agent as a layer within a combination of layers.

In some embodiments, the agent-containing compositions can be applied selectively to an abluminal surface of a medical device such as, for example, a stent. In most embodiments, the stent can be a balloon-expandable stent or a self-expandable stent. The "abluminal" surface refers to the surface of the device that is directed away from the lumen of the organ in which the device has been deployed. In one example, the lumen is an arterial lumen, and the abluminal surface of the stent is the surface that is placed in contact with the inner wall of the artery. Designing and applying predetermined IM profiles of agents within polymeric matrices to the abluminal surface of a medical device can provide a way for one of skill in the art to control the delivery of the agents within a subject and, thus, aid in preventing adverse effects and promoting desirable effects obtained from the agents.

Figure 5A:
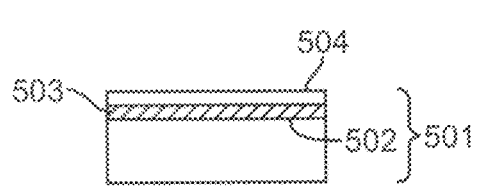
FIGS. 5a and 5b illustrate a sandwiched-coating design according to some embodiments of the present invention.
Figure 5B:
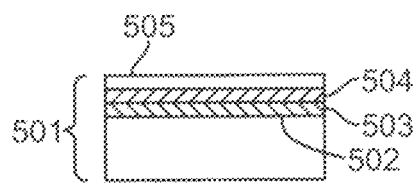

FIGS. 5a and 5b illustrate a sandwiched-coating design according to some embodiments of the present invention. FIG. 5a illustrates a cross-section of a stent strut 501 in which the abluminal surface 502 includes a first layer 503 containing agent B applied to the abluminal surface 502 and a second layer 504 containing agent A applied on the first layer 503 containing agent B. Each of the layers can be formed by any method known to one of skill in the art including, but not limited to, any one or any combination of the methods described above, and the layers can be applied to the entire stent or select regions of the stent.

In some embodiments, the first layer 503 can have an IM profile that is different from an IM profile in the second layer 504, such that agents A and B are delivered at different release rates, wherein the assumption can be that the difference between diffusion coefficients of the first layer 503 and second layer 504 is negligible. FIG. 5b illustrates a cross-section of the stent strut 501 in which the first layer 503 and the second layer 504 are coated by a third layer 505. The third layer 505 can contain any composition taught herein such as, for example, a topcoat to assist in controlling the rate of release of the agents, act as a biobeneficial layer, deliver one or more agents, or a combination thereof.

In some embodiments, each layer within the combination of layers can have a unique IM profile for each of the one or more agents, such that the combination of layers provides a controlled delivery of the one or more agents in a subject. In other embodiments, the combination of layers provides a step-by-step variation of IM profiles, the sum of which provides an overall IM profile of one or more agents within a medical device, coating, or a combination thereof.

Agent Morphology

The present invention also includes a method of obtaining an agent in a desired form, or a combination of forms, to create a medical article having a desired rate of release of the agent. The form of the agent can provide the selected rate of release through dissolution of the agent, diffusion of the agent, or a combination thereof. The form, or combination of forms, of the agent includes a component selected from a group consisting of a polymorph, a solvate, a hydrate, and an amorphous form of the agent. As described above, the medical article can include a stent or a coating for a stent.

Polymorphism can be defined as the ability of the same chemical substance to exist in different molecular packing arrangements. These different structures represent different thermodynamic stabilities and can be referred to as polymorphs, polymorphic modifications, or forms that are in a different polymorphic state. An example of polymorphs of the same substance is that of graphite and diamond, which are both made of carbon. Polymorphism is important in that each polymorph may provide a unique physicochemical property that can be exploited to improve the treatment of a subject by, for example, providing additional control over the rate of release of an agent from a medical article.

According to some embodiments, the method includes selecting a desired rate of release of an agent from the medical article and preparing a composition comprising a polymer and the agent. The composition is then applied to a surface of the medical article to form a polymeric layer comprising the agent; and a polymeric matrix having the selected rate of agent release is then formed from the polymeric layer, and any of the methods taught above can also be used to control the rate of release of the agent from the medical article.

The form of an agent can be chosen to provide varying solubilities to control the rate of dissolution of an agent from a medical article and into the bodily fluid or tissue of a subject. In some embodiments, polymorphs can be chosen to provide varying rates of diffusion through a bodily fluid by varying, for example, the size, shape, or distribution of an agent throughout a medical article. In some embodiments, polymorphs can be combined to provide a combination of desired dissolution and diffusion characteristics.

In some embodiments, the dissolution rate can be increased to shorten the time it takes to achieve a maximum concentration of an agent in a subject and/or to increase the maximum concentration of an agent that is obtainable in a subject at a given point in time, wherein a faster and more effective treatment with a particular agent may be possible. Likewise, a slower dissolution rate may be desired to lengthen the duration of the treatment and perhaps to reduce the amount of agent obtainable in a subject at a given point in time. In general, polymorphic forms of an agent can have a range of solubilities that differ by a factor ranging from above about 1 to above about 10 or above about 100 (e.g., a factor of about 2 or 3).

In some embodiments, where desirable, the agent can comprise any combination of forms, such as a combination of a polymorphic form and an amorphous form of the agent, wherein the polymorphic form is combined with the amorphous form in an amount that provides a predetermined dissolution rate in a subject receiving treatment. The ratios of the crystalline form verses the amorphous form can vary from 100% of one component to 100% of the other.

The agent can comprise a polymorphic form that is needle-shaped, rod-shaped, cubic, spherical, or a combination thereof, to provide a predetermined diffusion rate of the agent through the polymeric matrix. The size and shape of the agent, whether a polymorphic crystal or an amorphous form, can affect the movement of the agent through a polymeric matrix. For example, a polymorph that is needle or rod-shaped have a higher aspect ratio than a polymorph that is a cubic habit or irregular sphere and, thus, can be slower at moving through a polymer matrix. Because solubility of the agent is related to a polymorphic form of the agent, different polymorphs of the agent have differing solubilities.

The size and shape of the polymorph can be controlled, to a degree, through the method of particle formation. However, the size can also be modified through methods, such as ball milling or wet milling, both of which are methods well known to one of skill in the art. Micronizing will improve dissolution kinetics. Particle separations and fractionations can be performed using any method known to one of skill. The particle fractions can then be combined in any desired ratios to provide a polymer matrix having desired dissolution and diffusion characteristics.

In some embodiments, the agent is melted to obtain a melted form of the agent, and then the melted form is quenched to produce the desired form, or combination of forms, of the agent that provides the selected rate of release. In some embodiments, the agent is dissolved in a solvent to produce a solution containing the agent, and the solution is boiled to precipitate the agent into the desired form, or combination of forms, that provides the selected rate of release of the agent. In some embodiments, the desired form, or a combination of forms, comprises a metastable polymorphic form of the agent. Polymorphic forms can be characterized, for example, using optical microscopy, x-ray crystallography, infrared spectroscopy, differential scanning calorimetry, thermogravimetric analysis, electron microscopy, and atomic force microscopy.

EXAMPLES

The following examples are provided to further teach the concepts and embodiments of the present invention.

Example 1

The release of hydrophilic and hydrophobic agents can be controlled by combining particular agent and polymer characteristics to control the surface chemistry relationship between the components. Everolimus has a hydrophilic side chain and is released slower from a hydrophobic polymeric material such as poly(D,L-lactide) than a more hydrophilic polymeric material, such as a block copolymer of poly(butyl methacrylate) (PBMA) and poly(ethylene glycol) (PEG). Another hydrophilic polymer that is useful in the present invention is copolymer of poly(butylene terephthalate) (PBT) and PEG, otherwise known as PolyActive®. The effective diffusion coefficient of the PBMA-PEG can be changed, and the release of the everolimus controlled, through the application of a hydrophobic topcoat of poly(D,L-lactide) (d,l-PLA).

A hydrophobic agent such as, for example, paclitaxel can be encapsulated in a hydrophobic polymer or copolymer such as, for example, a poly(styrene-co-isobutylene-co-styrene) triblock copolymer and applied as a controlled volume. At a given loading of agent, the release rate of agent from such a morphology can be significantly lower using the hydrophobic encapsulating agent than using an a hydrophilic encapsulating such as, for example, poly(ethylene-co-vinyl alcohol).

Example 2

The path across which an agent must travel can be altered by altering the morphological profile of the polymer matrix. A gas phase boundary condition can be designed as a terminal step to control the initial morphology profile of a polymeric matrix. In this example, the gas phase composition contains water vapor and shows that humidity control during the coating process affects the final phase morphology of a hydrophobic polymer matrix that includes PBMA, D,L-PLA, or PVDF-HFP. The formation of rapid phase separation of the hydrophobic polymers by increasing the humidity as a terminal process step provides a faster release rate of an agent.

Figure 6:
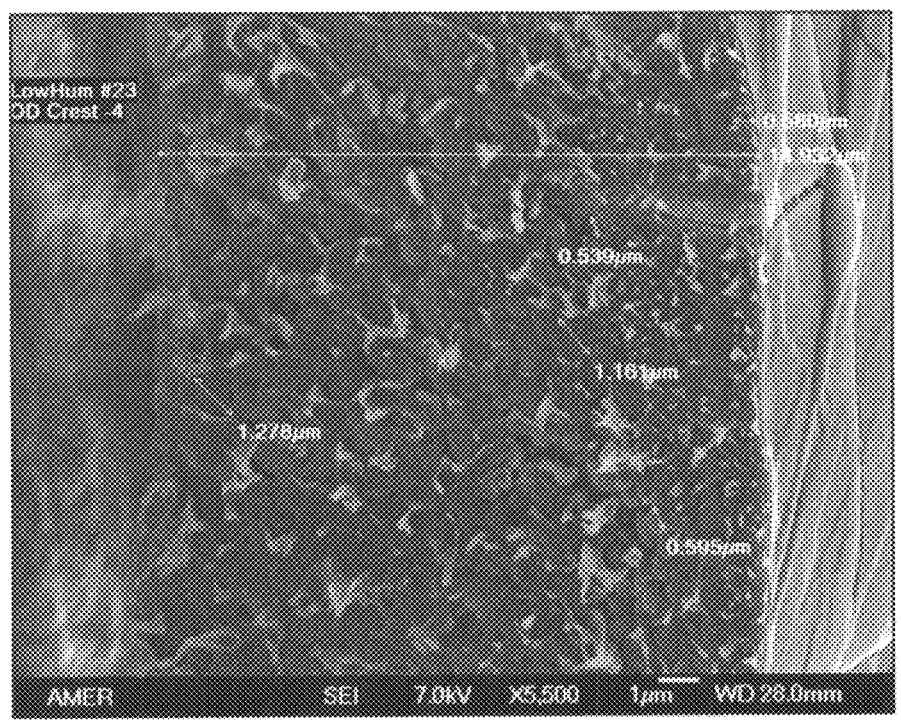
FIG. 6 illustrates an SEM of an IM profile at high magnification that was produced using a low humidity gas phase boundary condition according to some embodiments of the present invention.

FIG. 6 illustrates an SEM of an IM profile at high magnification that was produced using a low humidity gas phase boundary condition according to some embodiments of the present invention. In this example, the initial morphology (IM) profile of a coating processed using a designed terminal step was observed using scanning electron microscopy (SEM). A very thin coating of D,L-PLA (MW 65K) was combined with everolimus at a drug-to-polymer ratio (D/P) of 1:1 (w/w) in acetone. The composition was brush coated with a needle onto a stent and dried at room temperature under a boundary condition containing a low relative humidity of 20% to produce "the low humidity coating".

The IM profile shown in FIG. 6 is a cross-section of the coating showing darker regions that are drug-enriched domains. The smooth layer on right of the SEM is the zone of the phase separation, sometimes referred to as "the skin". The domain diameters are indicated by arrows—these domains are small domains and are percolated. Note that each domain seems to be covered by a thin layer, referred to as an "envelope" that can impede diffusion.

Figure 7A:
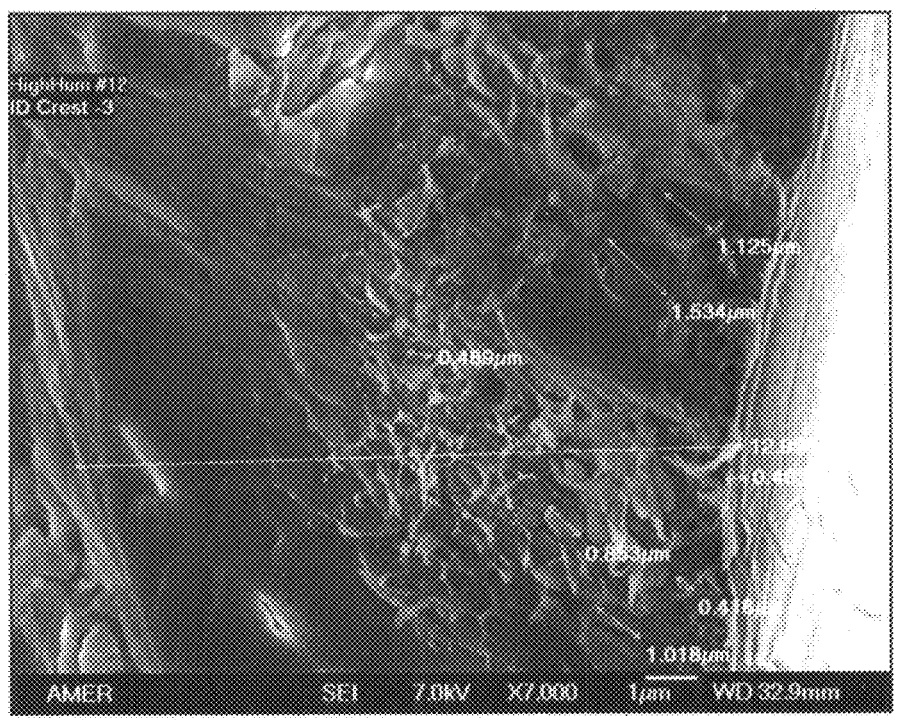
FIGS. 7a and 7b illustrate SEMs of an IM profile at high and low magnification that were produced using a high humidity gas phase boundary condition according to some embodiments of the present invention.
Figure 7B:
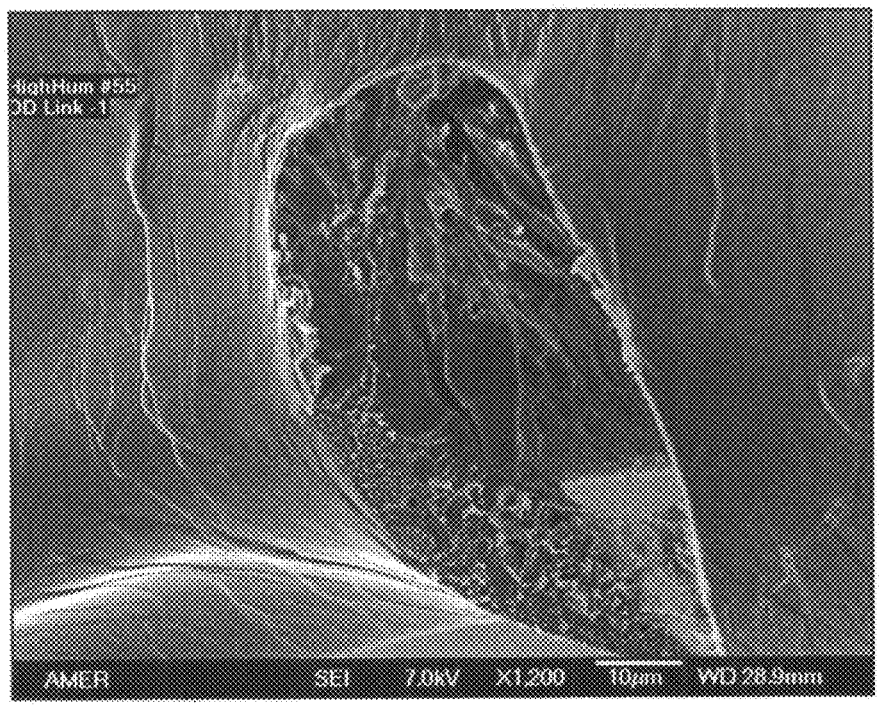

FIGS. 7a and 7b illustrate SEMs of an IM profile at high and low magnification that were produced using a high humidity gas phase boundary condition according to some embodiments of the present invention. In this example, the IM profile of the same coating was observed after using the same conditions and substituting only a high relative humidity for the low relative humidity to produce "the high humidity coating". The composition was brush coated with a needle onto a stent and dried at room temperature under a boundary condition containing a high relative humidity of 70%. In FIG. 7a, it becomes apparent that the distinctive domains that form under low relative humidity conditions are lost under high humidity conditions. In addition, larger regions of drug-enriched area are formed under high humidity conditions. Furthermore, although the domains remain percolated under high humidity conditions, they are more heterogeneous in size and have less envelope between domains that can impede diffusion. FIG. 7b is an SEM with lower magnification to better illustrate the increased heterogeneity in the sizes of the domains in the high humidity coating.

Example 3

Figure 8:
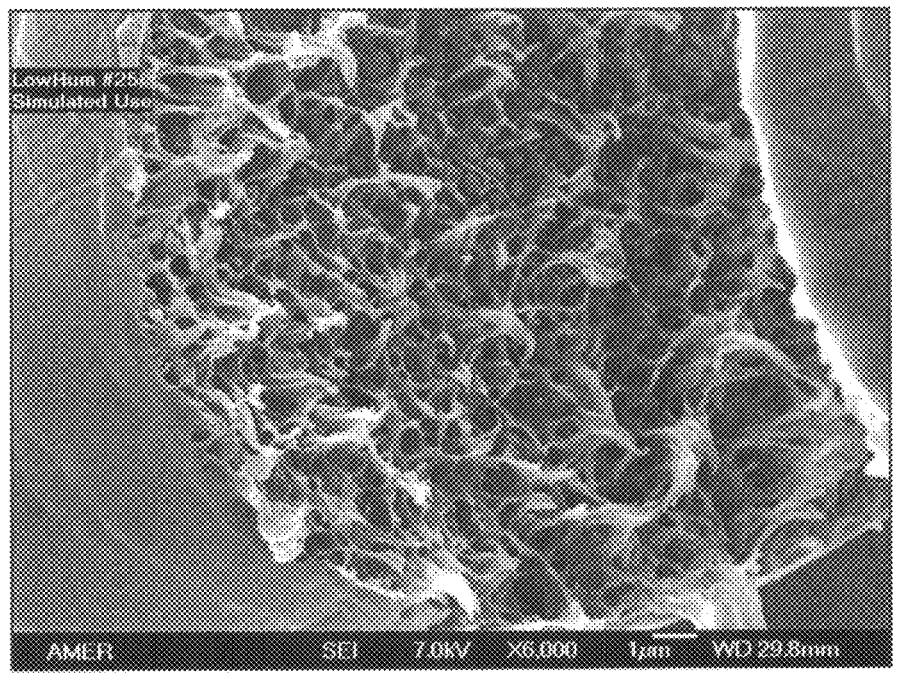
FIG. 8 illustrates an SEM of an IM profile at high magnification that was produced after exposing a coating produced using low humidity to a blood flow simulation using distilled water according to some embodiments of the present invention.

FIG. 8 illustrates an SEM of an IM profile at high magnification that was produced after exposing a coating produced using low humidity to a blood flow simulation using distilled water according to some embodiments of the present invention. The low humidity coating and high humidity coating of Example 2 were fluxed in water for 1 hour to highlight the change in morphology that occurs during agent release. Each coated stent was deployed in a hollow catheter and distilled water was allowed to flow past the stent for 1 hour at a flow rate of 50 ml/hr to simulate blood flow.

FIG. 8 shows that the drug-enriched domains are nearly gone after the hour of flux. The remaining material is the "envelope material" responsible for impeding diffusion due to the change in effective diffusion coefficient relative to the high humidity coating. A large amount of envelope material is left over because there were more small domains in the low humidity coating.

Figure 9A:
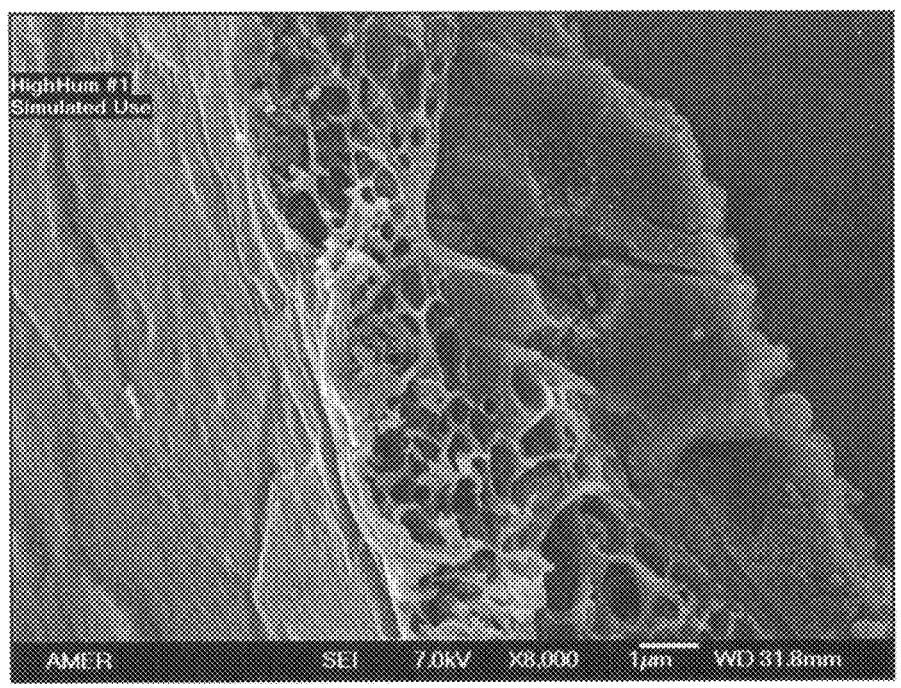
FIGS. 9a and 9b illustrate SEMs of an IM profile at high and low magnification, respectively, that were produced after exposing a coating produced using high humidity to a blood flow simulation using distilled water according to some embodiments of the present invention.
Figure 9B:
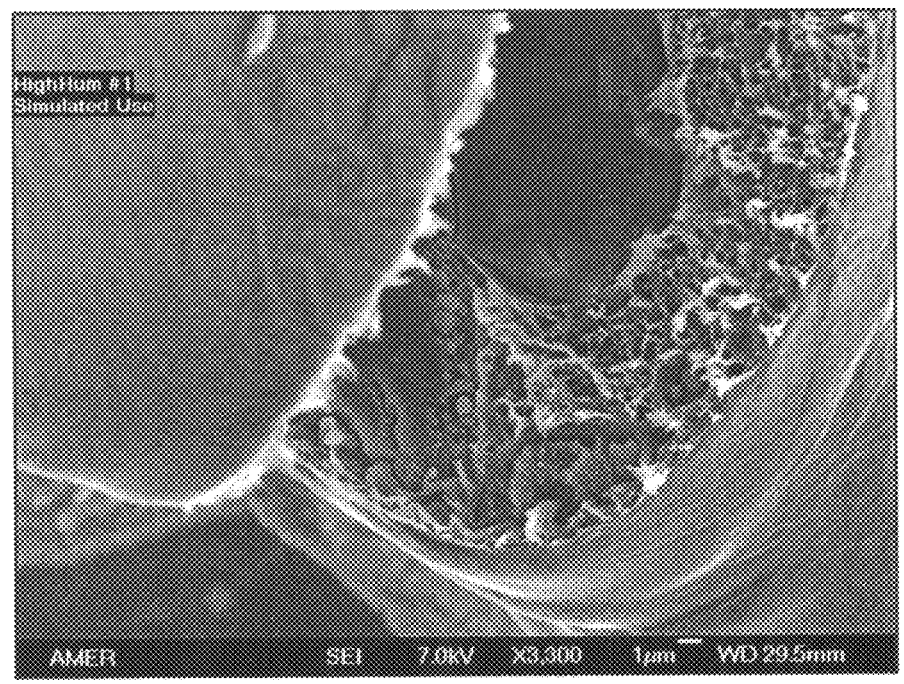

FIGS. 9a and 9b illustrate SEMs of an IM profile at high and low magnification, respectively, that were produced after exposing a coating produced using high humidity to a blood flow simulation using distilled water according to some embodiments of the present invention. The flux conditions used were the same as those used in FIG. 8. The high humidity coating has a faster release than the low humidity coating because there is less envelope material to impede diffusion and impede the formation of pores and channels throughout the coating. Note the homogeneity in the domain sizes—there are still small domains, and the diffusion has dominated in the larger domains.

Example 4

Figure 10A:
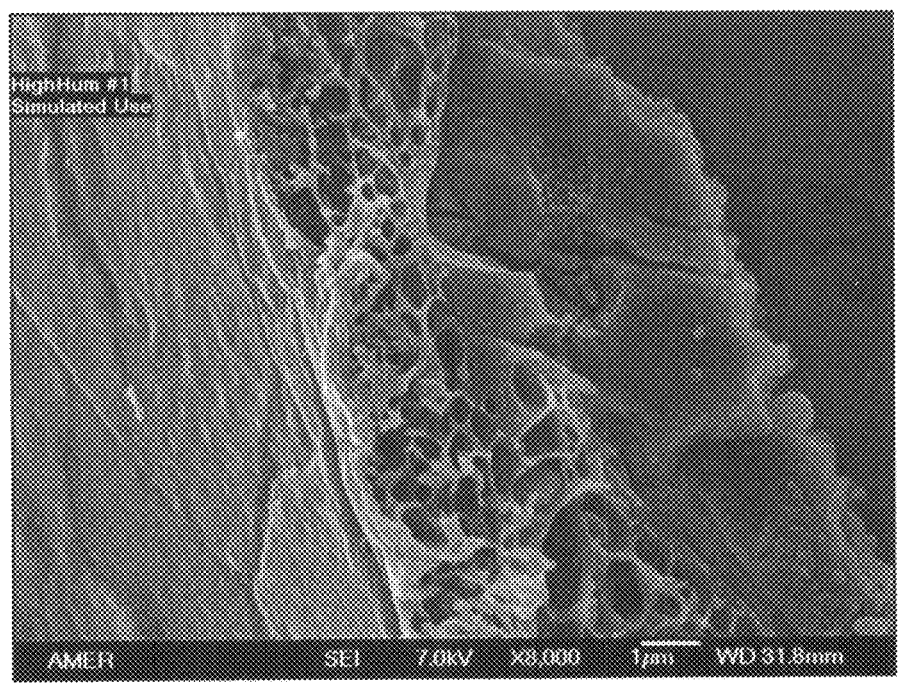
FIGS. 10a and 10b illustrate SEM photos of IM profiles that were produced after exposing coatings produced using low humidity conditions and high humidity conditions, respectively, to porcine serum for one day according to some embodiments of the present invention.
Figure 10B:
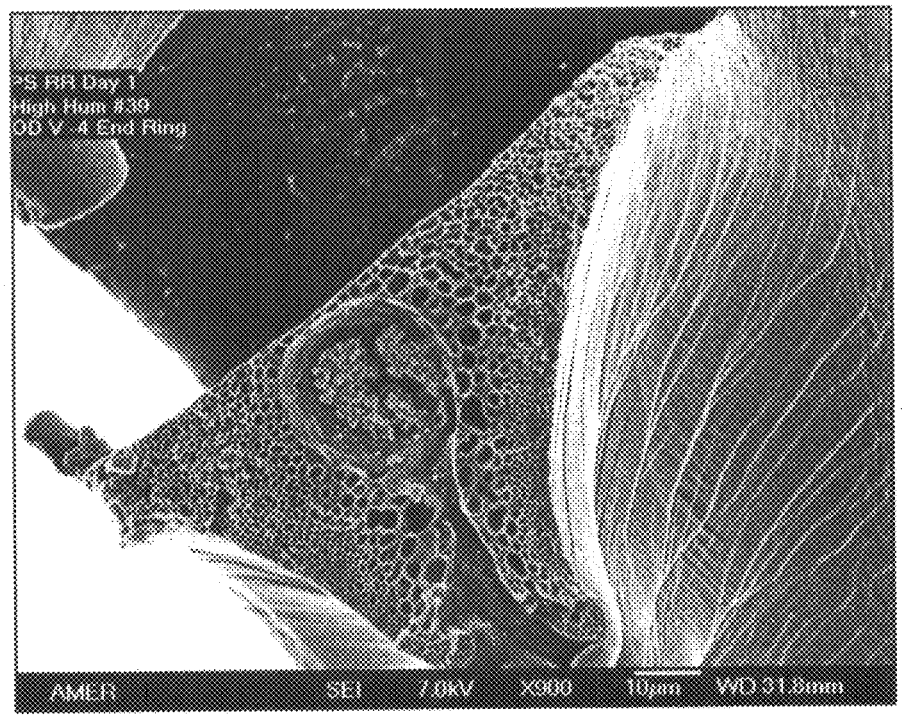

The rate of release of an agent from a polymeric matrix can be measured in vitro in a release medium, such as a buffered solution containing TRITON as a surfactant. FIGS. 10a and 10b illustrate SEM photos of IM profiles that were produced after exposing coatings produced using low humidity conditions and high humidity conditions, respectively, to a blood flow simulation using porcine serum according to some embodiments of the present invention. The low humidity coating and high humidity coating of Example 2 were fluxed in porcine serum at 37° C. to for 1 hour to simulate in vivo conditions and highlight the change in morphology that occurs during agent release. Each coated stent was deployed in a hollow conduit and porcine serum was allowed to flow past the stent for 1 hour at a flow rate of 50 ml/hr to simulate blood flow.

The images provided in these figures provide excellent illustrations of the differences in morphology between the low humidity coating and the high humidity coating. Again, these photos show that the coatings are percolated. Note also the homogeneity of the domain sizes in the low humidity coating and the relative heterogeneity of the domain sizes in the high humidity coating. These differences in morphology relate to the increase in envelope material in the low humidity coating that impedes diffusion and creates different diffusion coefficients between coatings.

Example 5

Figure 11A:
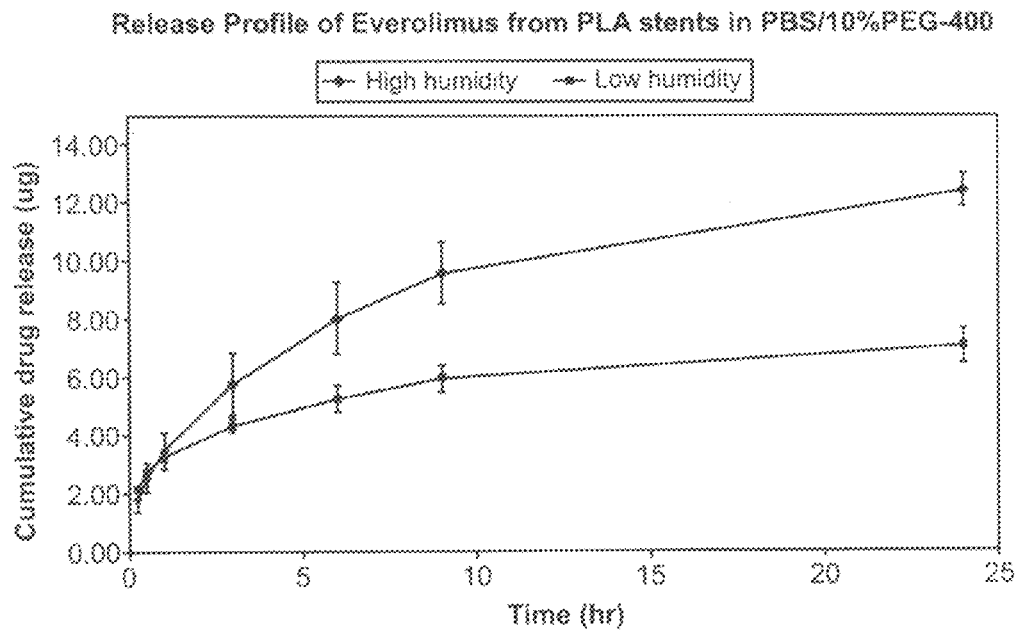
FIGS. 11a and 11b illustrate the agent release in a PBS/PEG solution and a porcine serum, respectively, from coatings produced using low humidity conditions and high humidity conditions, according to some embodiments of the present invention.
Figure 11B:
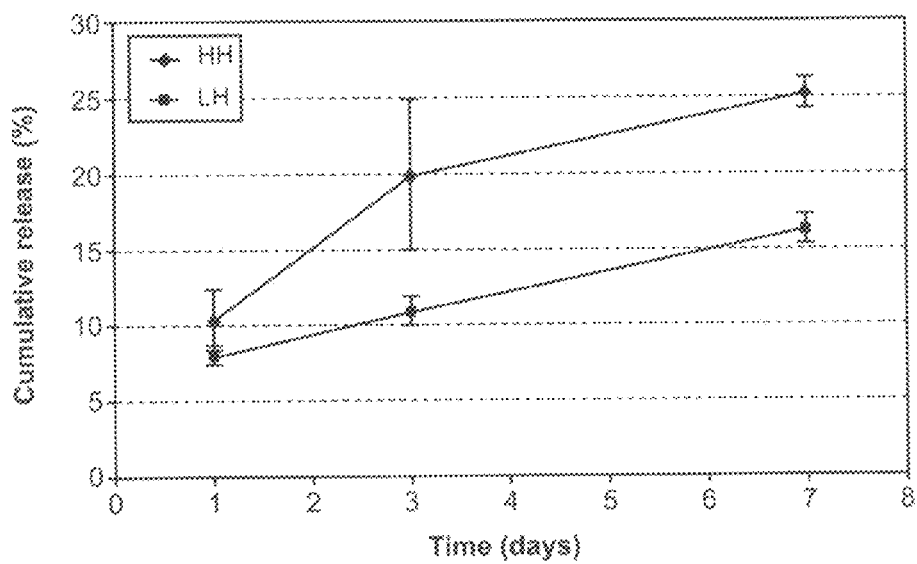

FIGS. 11a and 11b illustrate the agent release in a PBS(pH 7.4)/10% PEG solution and a porcine serum, respectively, for coatings produced using low humidity conditions and high humidity conditions, according to some embodiments of the present invention. The agent release rate was found to be higher initially in both solutions for the high humidity coating, and this higher rate of release continued for the first 3 days in the porcine serum. The release rate was about the same as the low humidity coating following 3 days in porcine serum.

Example 6

Release rate testing was performed on XIENCE® V stents at 4 hours and 24 hours of oven-drying time. These procedures include the series of oven-drying, crimping, pressing, split-molding, and sterilizing. "Crimping" is the process of using mechanical force to press the stent down onto a balloon. "Pressing" is the process of using mechanical force to press a stent down onto a balloon, while the stent and the balloon region are heated. "Split-molding" is the process of using heat and pressure for a specified time during which the diameter of the stent is radially constrained from expanding. In this example, the pressing was done at 70 psi at a temperature of 130° F., and the split-molding was done at a pressure of 300 psi, a temperature of 170° F., for a duration of 90 seconds.

Figure 12A:
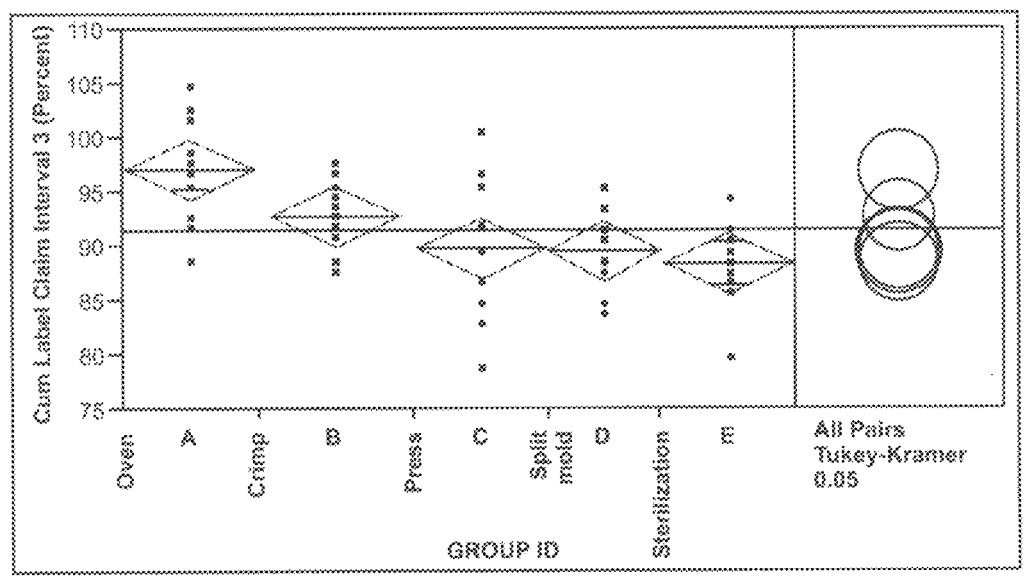
FIGS. 12a and 12b illustrate the effect of pressure and mechanical deformation on agent release according to some embodiments of the present invention.
Figure 12B:
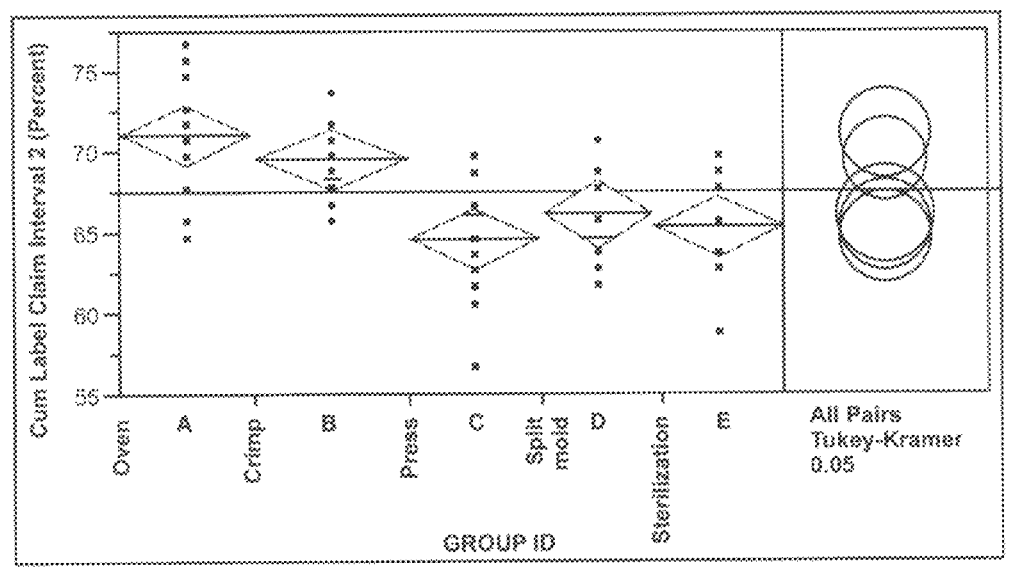

The release rates were measured using the porcine serum method of Example 4. For each of the drying time increments, the release rates were measured between oven-drying and crimping, between crimping and pressing, between pressing and split-molding, between split-molding and sterilization, and after sterilization. FIGS. 12a and 12b illustrate the effect of pressure and mechanical deformation on agent release according to some embodiments of the present invention. The results showed that processes that include the application of pressure and mechanical deformation reduce the release rate of the agent.

Example 7

Release rate testing was performed on CHAMPION DES stents with respect to the effect of pressure and temperature, but with particular attention to the added effect of temperature. The CHAMPION DES system uses a PLA polymer for delivery of the agent. In this example, the pressing was done at 70 psi at a temperature of 130° F., and the heat set was done at a pressure of 300 psi, a temperature of 55° C., for a duration of 10 minutes.

Figure 13A:
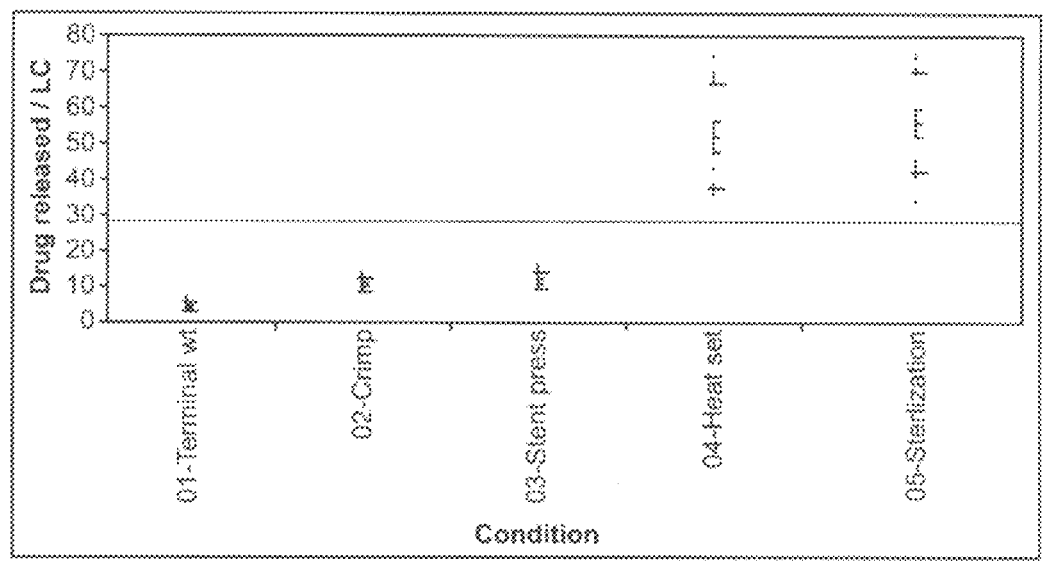
FIGS. 13a and 13b illustrate the effect of pressure and temperature on the release rate of an agent according to some embodiments of the present invention.
Figure 13B:
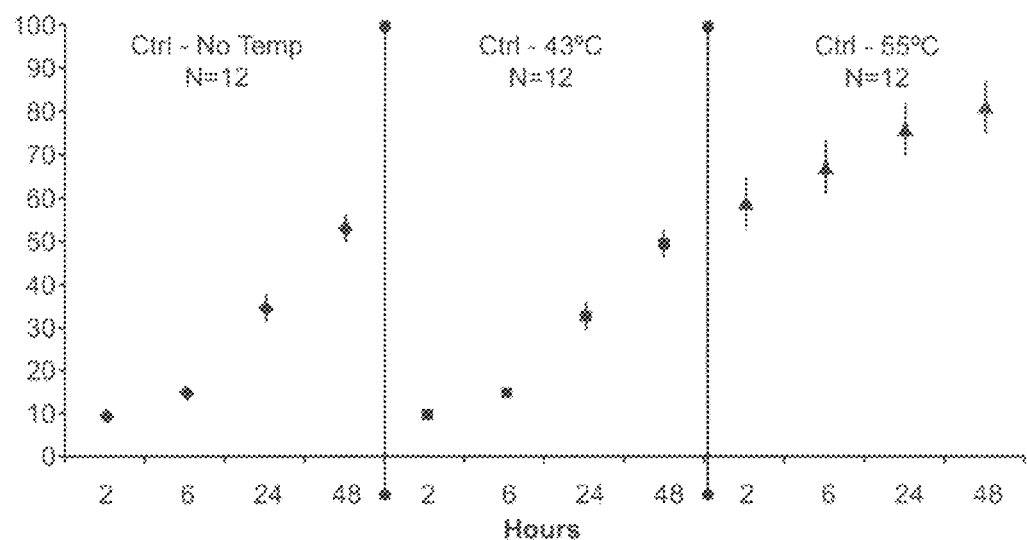

FIGS. 13a and 13b illustrate the effect of pressure and temperature on the release rate of an agent according to some embodiments of the present invention. FIG. 13a illustrates that the release rate doubled after crimping, showing that the use of a mechanical pressure can increase the release rate. However, the combined application of pressure and heat for a duration of time increased the release rate to a much greater extent, highlighting the dramatic effect of the addition of heat for a duration of time on the rate of agent release from a stent. (Note that the term "heat set" is used in FIG. 13a to indicate a process similar to the split-molding process, in which the balloon is pressurized and heated while the stent is radially constrained from expanding). FIG. 13b illustrates that the temperature at which the heat set is performed can have a dramatic effect on the amount of agent released as well, showing that as the temperature is increased from 43° C. to 55° C., the release rate can increase by about 500% due to these process conditions.

Example 8

Polymorphs of estradiol can be prepared and used to obtain varying agent delivery rates. Estradiol hemihydrate can be obtained from Sigma Chemical Co Anhydrous forms of estradiol can be prepared by melting the estradiol hemihydrate and slow cooling the melt to obtain a first polymorph (P1). A second polymorph (P2) can be prepared by melting the estradiol hemihydrate and rapidly cooling the melt by quenching the melt in liquid nitrogen. The second polymorph can also be prepared by boiling the estradiol hemihydrate in an ethyl acetate solution and crystallizing P2 from the solution. Both methods of producing P2 should produce a polymorph with identical characteristics.

The polymorphic crystals can be combined into a polymeric material, and each preparation can be distinguished from the remainder of the substance (e.g. solvates, and not true polymorphs) by viewing them as solid dispersions under crossed polarizers, where the crystals will be brighter compared to the remainder of the substance. The crystals of estradiol should include needle-like crystals having dimensions ranging in size from 4-11 µm. One means of distinguishing between P1 and P2 is to use Raman spectroscopy, where the two forms should be distinguishable by a splitting of the C17-O peak at 1284 cm$^{-1}$ and 1294 cm$^{-1}$, which is evidence of the presence and absence of hydrogen bonding at the hydroxyl group of position 17.

While particular embodiments of the present invention have been shown and described, those skilled in the art will note that variations and modifications can be made to the present invention without departing from the spirit and scope of the teachings. A multitude of embodiments that include a variety of chemical compositions, polymers, agents and methods have been taught herein. One of skill in the art is to appreciate that such teachings are provided by way of example only and are not intended to limit the scope of the invention. The embodiments for the IM profiles that are taught herein are not meant to be limiting, since the IM profiles possible are virtually limitless in variety. The IM profiles taught in the present invention can be incorporated into any medical article.

We claim:

1. A method comprising:
obtaining a medical device with a polymeric coating layer, the polymeric coating layer having been dried;
applying a pressure greater than ambient to the dried polymeric layer of the medical device using a pressure vessel; and
optionally applying heat to the dried polymeric layer of the medical device in combination with the application of the pressure.

2. The method of claim 1, wherein the pressure is pulsed.

3. The method of claim 1, wherein the polymeric coating layer comprises at least one polymer selected from the group consisting of poly(hydroxyalkanoates) (PHAs), poly(ester amides) (PEAs), poly(hydroxyalkanoate-co-ester amides), polyesters, polyacrylates, polymethacrylates, polycaprolactones, polyglycolides, poly(ethylene glycol) (PEG), poly(propylene glycol) (PPG), poly(ethylene oxide) (PEO), poly(propylene oxide) (PPO), poly(propylene fumarate) (PPF), poly(D-lactide), poly(L-lactide), poly(D,L-lactide), poly(meso-lactide), poly(L-lactide-co-meso-lactide), poly(D-lactide-co-meso-lactide), poly(D,L-lactide-co-meso-lactide), poly(D,L-lactide-co-PEG), poly(D,L-lactide-co-trimethylene carbonate), poly(lactide-co-glycolide), poly(glycolic acid-co-trimethylene carbonate), poly(trimethylene carbonate), PHA-PEG, PBT-PEG (PolyActive®), PEG-PPO-PEG (Pluronic®), and PPF-co-PEG.

4. The method of claim 1, wherein the polymeric layer comprises at least one copolymer, the copolymer being formed from at least one monomer of the group consisting of methyl methacrylate, hydroxyethyl methacrylate, butyl methacrylate, lauryl methacrylate, glycidyl methacrylate, and PEG-methacrylate.

5. The method of claim 1, wherein the medical device comprises an agent.

6. The method of claim 5, wherein the agent is selected from the group consisting of poly(alkylene glycols), phosphorylcholine, poly(N-vinyl pyrrolidone), poly(ethylene oxide), poly(acrylamide methyl propane sulfonic acid), poly(styrene sulfonate), polysaccharides, poly(ester amides), peptides, non-thrombotics, antimicrobials, nitric oxide donors, free radical scavengers, and combinations thereof.

7. The method of claim 6, wherein the poly(alkylene glycol) comprises a component selected from the group consisting of poly(ethylene glycol)(PEG), poly(propylene glycol)(PPG), a PEG-PPG copolymer, and combinations thereof.

8. The method of claim 6, wherein the polysaccharide comprises a component selected from the group consisting of carboxymethylcellulose, sulfonated dextran, sulfated dextran, dermatan sulfate, chondroitin sulfate, hyaluronic acid, heparin, hirudin, and combinations thereof.

9. The method of claim 6, wherein the peptide comprises a component selected from the group consisting of elastin, silk-elastin, collagen, atrial natriuretic peptide (ANP), Arg-Gly-Asp (RGD), and any salts thereof, and combinations thereof.

10. The method of claim 6, wherein the free radical scavenger comprises a component selected from the group consisting of 2,2',6,6'-tetramethyl-1-piperinyloxy, free radical; 4-amino-2,2',6,6'-tetramethyl-1-piperinyloxy, free radical; 4-hydroxy-2,2',6,6'-tetramethyl-piperidene-1-oxy, free radical; 2,2',3,4,5,5'-hexamethyl-3-imidazolinium-1-yloxy methyl sulfate, free radical; 16-doxyl-stearic acid, free radical; and combinations thereof.

11. The method of claim 6, wherein the nitric oxide donor comprises a component selected from the group consisting of S-nitrosothiols, nitrites, N-oxo-N-nitrosamines, diazenium diolates, and any salts thereof, and combinations thereof.

12. The method of claim 5, wherein the agent is selected from the group consisting of rapamycin, methyl rapamycin, everolimus, pimecrolimus, 42-Epi-(tetrazoylyl)-rapamycin (ABT-578), tacrolimus, and any salts thereof, and combinations thereof.

13. The method of claim 5, wherein the agent is selected from the group consisting of imatinib mesylate, paclitaxel, docetaxel, midostaurin, and any salts thereof, and combinations thereof.

14. The method of claim 5, wherein the agent comprises a component selected from a group consisting of estradiol, clobetasol, idoxifen, tazarotene, and combinations thereof.

15. The method of claim 5, wherein the medical device comprises a combination of agents, the combination of agents being everolimus and clobetasol, tacrolimus and rapamycin, tacrolimus and everolimus, or rapamycin and paclitaxel, or any combination thereof.

16. The method of claim 5, wherein the polymeric layer comprises at least some of the agent.

17. The method of claim 5, wherein the application of the pressure, or the application of the combination of heat and the pressure, alters the release rate of the agent from the medical device.

18. A method comprising:
obtaining a medical device with a polymeric coating layer, the polymeric coating layer having been dried;
applying a pressure greater than ambient to the dried polymeric layer of the medical device using a pressure vessel, the pressure sufficient to create a mechanical deformation of the polymeric layer of the medical device; and optionally applying heat to the dried polymeric layer of the medical device in combination with the application of the pressure.

19. The method of claim 18, wherein the pressure is pulsed.

* * * * *